US010815506B2

(12) United States Patent
Rancke-Madsen et al.

(10) Patent No.: US 10,815,506 B2
(45) Date of Patent: Oct. 27, 2020

(54) PRODUCTION OF FATTY ACID ALKYL ESTERS WITH CAUSTIC TREATMENT

(71) Applicant: Novozymes A/S, Bagsvaerd (DK)

(72) Inventors: Anders Rancke-Madsen, Charlottelund (DK); Per Munk Nielsen, Hilleroed (DK)

(73) Assignee: Novozymes A/S, Bagsvaerd (DK)

( * ) Notice: Subject to any disclaimer, the term of this patent is extended or adjusted under 35 U.S.C. 154(b) by 321 days.

(21) Appl. No.: 15/312,230

(22) PCT Filed: May 28, 2015

(86) PCT No.: PCT/EP2015/061872
§ 371 (c)(1),
(2) Date: Nov. 18, 2016

(87) PCT Pub. No.: WO2015/181308
PCT Pub. Date: Dec. 3, 2015

(65) Prior Publication Data
US 2017/0081683 A1    Mar. 23, 2017

(30) Foreign Application Priority Data

May 28, 2014 (EP) .................................... 14170447
Jul. 3, 2014 (EP) .................................... 14175592

(51) Int. Cl.
*C12P 7/64* (2006.01)
*C11C 1/00* (2006.01)
*C11C 3/08* (2006.01)
*C12N 9/20* (2006.01)

(52) U.S. Cl.
CPC ................ *C12P 7/649* (2013.01); *C11C 1/00* (2013.01); *C11C 3/08* (2013.01); *C12N 9/20* (2013.01); *C12Y 301/01003* (2013.01); *Y02E 50/13* (2013.01)

(58) Field of Classification Search
CPC ...... C11C 1/00; C11C 3/08; C12N 9/20; C12P 7/649; C12Y 301/01003; Y02E 50/13
See application file for complete search history.

(56) References Cited

U.S. PATENT DOCUMENTS

2008/0118961 A1* 5/2008 Sato .................. C11B 13/02
435/134

FOREIGN PATENT DOCUMENTS

| WO | 2006/050589 A1 | 5/2006 | |
| WO | WO-2006050589 A1 * | 5/2006 | ............. C11B 13/02 |
| WO | 2006/072256 A2 | 7/2006 | |
| WO | 2011/107977 A1 | 9/2011 | |
| WO | WO-2011107977 A1 * | 9/2011 | ............. C11C 3/003 |
| WO | 2012/098114 A1 | 7/2012 | |
| WO | WO-2012098114 A1 * | 7/2012 | ............. C12P 7/649 |
| WO | 2013/030816 A1 | 3/2013 | |
| WO | WO-2013030816 A1 * | 3/2013 | ............... C12P 7/64 |

OTHER PUBLICATIONS

Cesarini et al. (2014) Biotechnology for Biofuels 7(1): 29 (Year: 2014).*
Haas et al. (1996) J. Am. Oil Chemists' Society 73(11): 1393-1401. (Year: 1996).*
Cesarini et al, 2014, Biotechnol Biofuels, vol. 7, No. 1, p. 29.
Haas et al, 1997, J Amer Oil Chem Soc, vol. 73, pp. 1393-1401.
Lv et al, 2010, Proc Biochem, vol. 45, pp. 446-450.

* cited by examiner

*Primary Examiner* — Lisa J Hobbs
(74) *Attorney, Agent, or Firm* — Elias Lambiris

(57) ABSTRACT

A method for producing fatty acid alkyl esters, comprising providing a system comprising an oil phase/hydrophobic phase an a hydrophilic phase, and reacting a fatty acid feedstock present in said oil phase/hydrophobic phase with alcohol in the presence of water and one or more lipolytic enzymes.

14 Claims, 2 Drawing Sheets
Specification includes a Sequence Listing.

PRODUCTION OF FATTY ACID ALKYL ESTERS WITH CAUSTIC TREATMENT

CROSS-REFERENCE TO RELATED APPLICATIONS

This application is a 35 U.S.C. 371 national application of PCT/EP2015/061872 filed May 28, 2015 which claims priority or the benefit under 35 U.S.C. 119 of European application nos. 14170447.8 and 14175592.6 filed May 28, 2014 and Jul. 3, 2014, the contents of which are fully incorporated herein by reference.

REFERENCE TO A SEQUENCE LISTING

This application contains a Sequence Listing in computer readable form. The computer readable form is incorporated herein by reference.

FIELD OF THE INVENTION

The present invention relates to a method for producing fatty acid alkyl esters from fatty acid feedstock. In the method according to the invention includes a polishing reaction wherein alkaline agent or base is mixed directly in to the full enzymatic reaction mixture.

BACKGROUND ART

Fatty acid alkyl esters may be used as fuel, biodiesel, in standard diesel engines. Biodiesel can be used alone, or blended with fossil diesel. Biodiesel has become more attractive recently because of its environmental benefits.

Although biodiesel is at present primarily produced chemically (using e.g., NaOH and/or sodium methoxide as catalyst), there are several associated problems to restrict its development, such as pre-processing of oil due to high contents of free fatty acids, need for high alcohol surplus in reaction removal of chemical catalyst from ester and glycerol phase, and removal of inorganic salts during glycerol recovery.

The disadvantages caused by chemical catalysts are largely prevented by using lipolytic enzymes as the catalysts and in recent years interest has developed in the use of lipases in transesterification for the production of biodiesel.

Biodiesel produced by enzymatic bioconversion is, compared with chemical conversion, more environmental friendly. However, with very few exceptions, enzyme technology is not currently used in commercial scale biodiesel production.

Processes for enzymatic production of fatty acid alkyl esters using liquid enzymes are described in e.g., WO 2006/072256, Lv et al. (Process Biochemistry 45 (2010) 446-450) and WO2012/098114.

In processes for production of fatty acid alkyl esters or biodiesel, a fatty acid feedstock is reacted with alcohol, typically methanol, to produce the fatty acid alkyl esters and glycerol. The processes include additional steps, such as caustic treatment of the fatty acid alkyl esters to reduce the amounts of free fatty acids. Prior to such processing steps, the oil phase/hydrophobic phase containing the fatty acid alkyl esters, free fatty acids etc. is separated from the hydrophilic phase containing e.g. water, glycerol and a part of excess alcohol. Separation of the oil phase/hydrophobic phase and hydrophilic phase prior to caustic treatment is considered necessary, mainly because it is believed that the glycerol formed as a by-product of the production of fatty acid alkyl esters, will contain large amounts of salts, absent phase separation prior to caustic treatment. This is undesirable, because the glycerol itself is a valuable by-product, which is usually processed into technical grade glycerol.

Further, it is considered advantageous to separate the oil phase/hydrophobic phase and the hydrophilic phase prior to caustic treatment in order to reduce evaporation of alcohol because caustic treatment is performed at elevated temperatures, near the boiling point of the alcohol.

Finally, when the fatty acid alkyl esters/biodiesel is produced by enzymatic bioconversion, phase separation prior to caustic treatment makes it possible to re-use much of the enzyme, which would otherwise denature at least in part, during caustic treatment.

However, during separation of the oil phase/hydrophobic phase form the hydrophilic phase, a third emulsion phase is formed, which also contains some fatty acid alkyl esters or biodiesel. This third phase is not collected together with the oil phase/hydrophobic phase. Hence, besides offering technical challenges, the separation step also causes loss of fatty acid alkyl esters or biodiesel.

Therefore, there is a need for more efficient processes for production of fatty acid alkyl esters or biodiesel.

SUMMARY OF THE INVENTION

The invention provides a process for production of fatty acid alkyl esters by reacting a fatty acid feedstock with an alcohol in a system comprising an oil phase/hydrophobic phase and a hydrophilic phase, wherein soap/salts are formed from free fatty acids by treatment with one or more alkaline agents, in the presence of said alcohol/said hydrophilic phase.

The invention also provides a process for production of fatty acid alkyl esters, comprising
  i) providing a system comprising an oil phase/hydrophobic phase and a hydrophilic phase, and
  ii) reacting a fatty acid feedstock present in said oil phase/hydrophobic phase with alcohol in the presence of water and one or more lipolytic enzymes;
wherein the total amount of said one or more lipolytic enzymes is within the range of 100 to 500 enzyme units/g oil phase/hydrophobic phase.

An advantage of the process of the invention is that very little product, i.e. fatty acid esters/biodiesel, is lost during the process, which provides an economic benefit and increased sustainability. A further advantage is that the process operations have been considerably simplified.

In a further aspect, the invention provides a composition comprising at least 90% (w/w) fatty acid alkyl esters, from 300 to 400 ppm soap, less than 0.25% (w/w) free fatty acids and less than 0.23% (w/w) glycerides.

Figure 1:
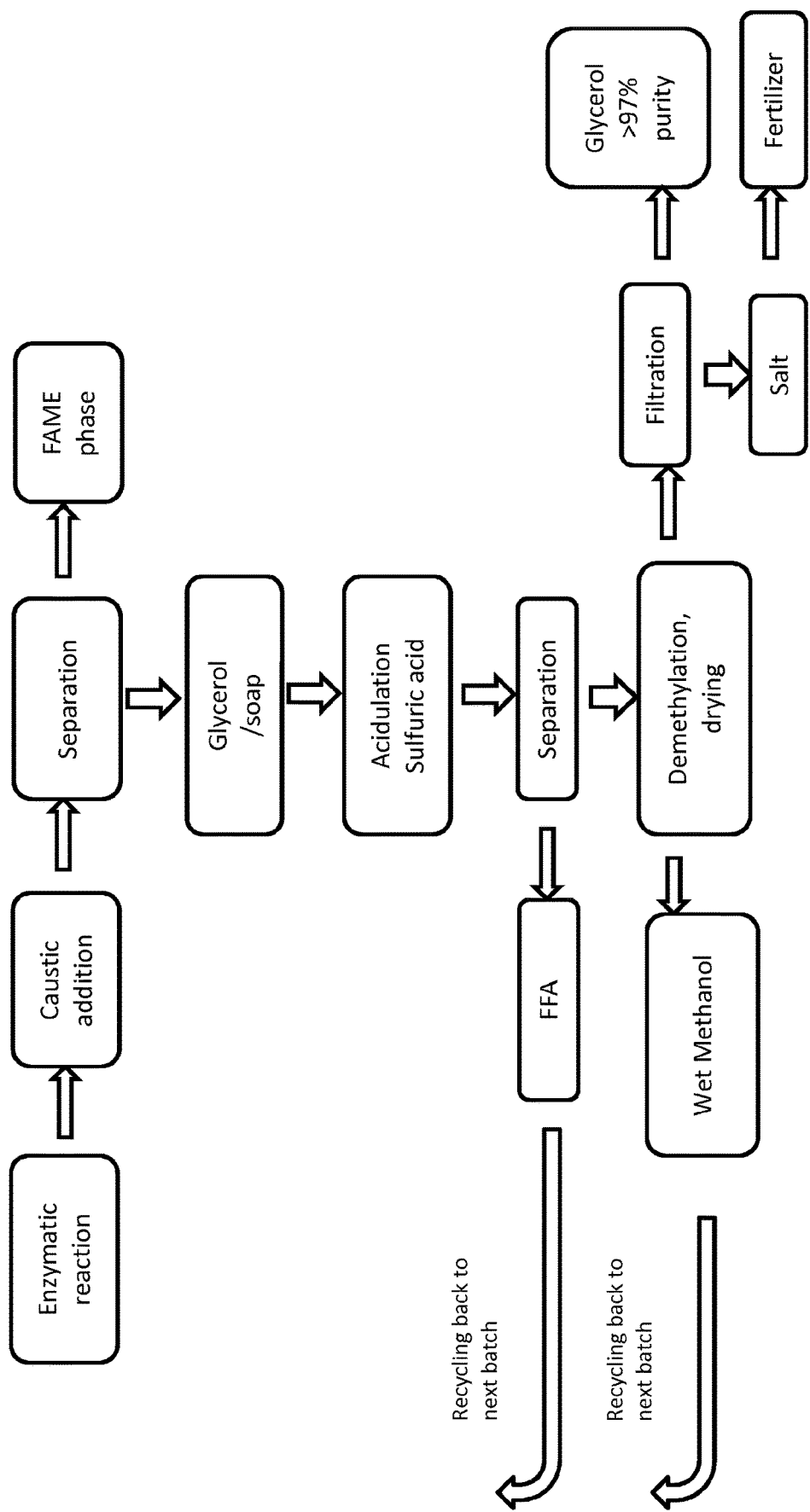
FIG. 1: shows a schematic outline of the process according to the invention, including preparation of an oil phase/hydrophobic phase having a high content fatty acid esters (FAME phase), which is separated from a hydrophilic phase containing glycerol, alcohol and soap/salts of residual fatty acids (Glycerol/soap phase); acidification of the soap/fatty acid salts to produce free fatty acids which may be recycled and used as fatty acid feedstock in the enzymatic reaction; and production of high grade/tech grade glycerol.
Figure 2:
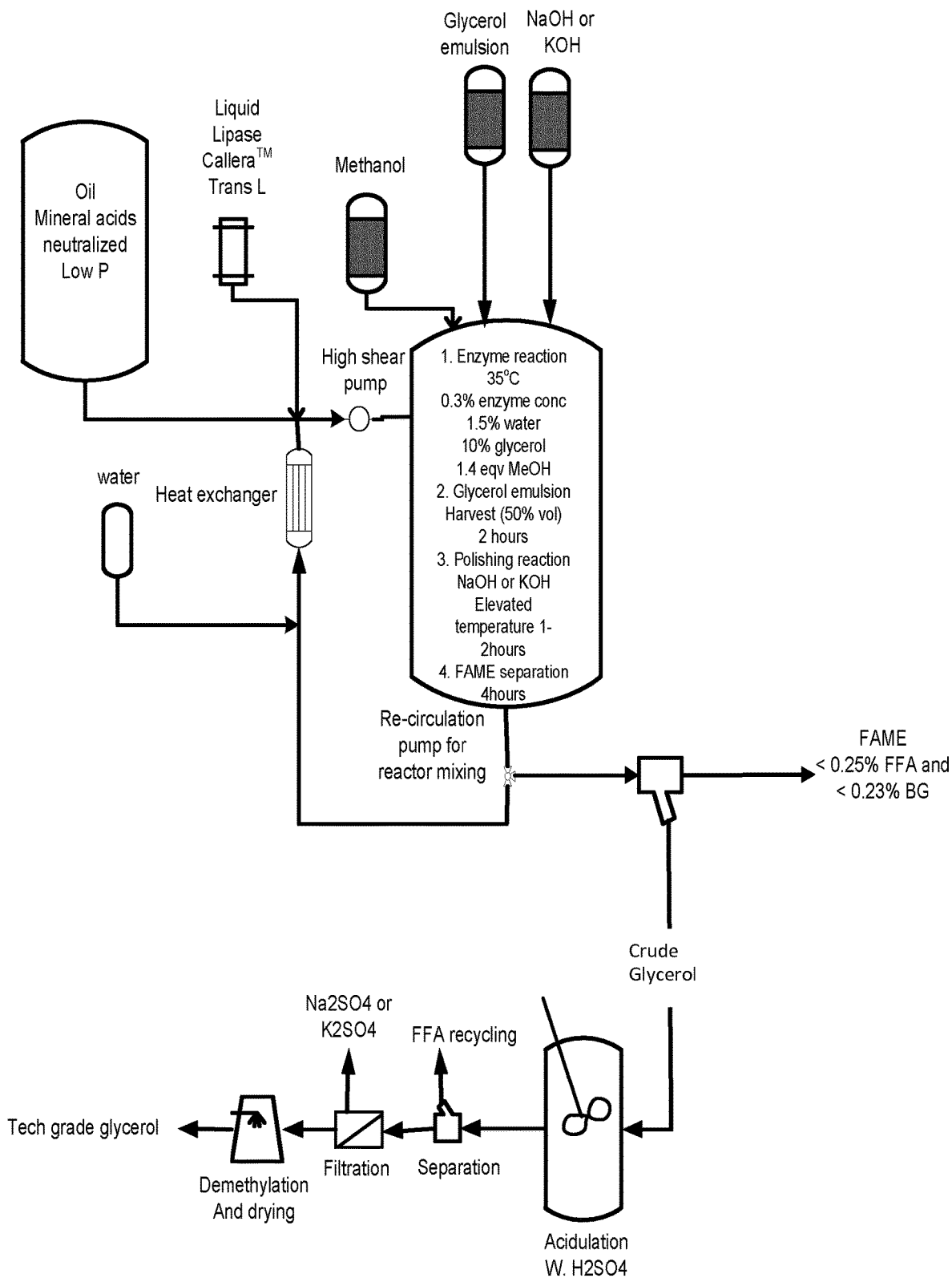
FIG. 2: shows an embodiment of a process of the invention. The figure shows a process flow sheet for a batch operation plant. In the particular embodiment, the reaction system comprises 1% water, 10% glycerol, 1.4 eqv. MeOH and 0.3% enzyme (lipase), which corresponds to 300 lipase units/g oil phase/hydrophobic phase. The plant can be constructed also as a continuous stirred tank reactor system.

The figures have been included for illustration purposes alone and should in no way be construed as limiting the invention.

DETAILED DESCRIPTION OF THE INVENTION

Definitions

Biodiesel: Fatty acid alkyl esters (FAAE) of short-chain alcohols, such as fatty acid methyl esters (FAME) and fatty acid ethyl esters (FAEE) are also called biodiesel, because they are used as an additive to or as replacement of fossil diesel.

Alcohol: The alcohol used in the method of the invention is preferably a short-chain alcohol having 1 to 5 carbon atoms ($C_1$, $C_2$, $C_3$, $C_4$, or $C_5$).

Fatty acid feedstock: The term "fatty acid feedstock" is defined herein as a substrate comprising triglyceride, diglyceride, monoglyceride, free fatty acid or any combination thereof. In principle, any oils and fats of vegetable or animal origin comprising fatty acids may be used as substrate for producing fatty acid alkyl esters in the process of the invention.

Lipolytic Enzyme

The one or more lipolytic enzyme applied in the method of the present invention is selected from lipases, phospholipases, cutinases, acyltransferases or a mixture of one and more of lipase, phospholipase, cutinase and acyltransferase. The one or more lipolytic enzyme is selected from the enzymes in EC 3.1.1, EC 3.1.4, and EC 2.3. The one or more lipolytic enzyme may also be a mixture of one or more lipases. The one or more lipolytic enzyme may include a lipase and a phospholipase. The one or more lipolytic enzyme includes a lipase of EC 3.1.1.3. The one or more lipolytic enzyme includes a lipase having activity on tri-, di-, and monoglycerides.

Lipases: A suitable lipolytic enzyme may be a polypeptide having lipase activity, e.g., one selected from the *Candida antarctica* lipase A (CALA) as disclosed in WO 88/02775, the *C. antarctica* lipase B (CALB) as disclosed in WO 88/02775 and shown in SEQ ID NO:1 of WO2008065060, the *Thermomyces lanuginosus* (previously *Humicola lanuginosus*) lipase disclosed in EP 258 068), the *Thermomyces lanuginosus* variants disclosed in WO 2000/60063 or WO 1995/22615, in particular the lipase shown in positions 1-269 of SEQ ID NO: 2 of WO 95/22615, the *Hyphozyma* sp. lipase (WO 98/018912), and the *Rhizomucor miehei* lipase (SEQ ID NO:5 in WO 2004/099400), a lipase from *P. alcaligenes* or *P. pseudoalcaligenes* (EP 218 272), *P. cepacia* (EP 331 376), *P. glumae*, *P. stutzeri* (GB 1,372,034), *P. fluorescens*, *Pseudomonas* sp. strain SD 705 (WO 95/06720 and WO 96/27002), *P. wisconsinensis* (WO 96/12012); a *Bacillus* lipase, e.g., from *B. subtilis* (Dartois et al. (1993), Biochemica et Biophysica Acta, 1131, 253-360), *B. stearothermophilus* (JP 64/744992) or *B. pumilus* (WO 91/16422). Also preferred is a lipase from any of the following organisms: *Fusarium oxysporum, Absidia reflexa, Absidia corymbefera, Rhizomucor miehei, Rhizopus delemar* (oryzae), *Aspergillus niger, Aspergillus tubingensis, Fusarium heterosporum, Aspergillus oryzae, Penicilium camembertii, Aspergillus foetidus, Aspergillus niger, Aspergillus oryzae* and *Thermomyces lanuginosus*, such as a lipase selected from any of SEQ ID NOs: 1 to 15 in WO 2004/099400.

A lipase which is useful in relation to the present invention is a lipase having a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or even 100% sequence identity to the polypeptide shown in positions 1-269 of SEQ ID NO: 2 of WO 95/22615 or to the polypeptide shown in SEQ ID NO:1 of WO2008/065060.

Commercial lipase preparations suitable for use in the process of the invention include LIPOZYME CALB L, LIPOZYME® TL 100L and CALLERA™ TRANS (all available from Novozymes A/S).

Particularly useful lipases may be selected from the group consisting of
 (a) a polypeptide comprising or consisting of the amino acid sequence set forth in SEQ ID NO: 1 or SEQ ID NO: 2;
 (b) a polypeptide which is a subsequence of the amino acid sequence set forth in SEQ ID NO: 1 or 2;
 (c) a polypeptide having at least 60% sequence identity, such as e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, to any of the polypeptides defined in (a) and (b).

The lipase set forth in (c) may be a variant the amino acid sequence set forth in SEQ ID NO: 1, wherein the polypeptide comprises the following substitutions T231R and N233R.

The lipase set forth in item (c) may have an amino acid sequence which differs by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 from the polypeptide of SEQ ID NO: 1 or 2.

The lipase may be a variant of a parent lipase, which variant has lipase activity and has at least 60%, such at least 65%, at least 70%, at least 75%, at least 80%, at least 85%, at least 90%, at least 95% identity, at least 96%, at least 97%, at least 98%, or at least 99%, but less than 100% sequence identity with SEQ ID NO: 1, and comprises substitutions at positions corresponding to T231R+N233R and at least one or more (e.g., several) of D96E, D111A, D254S, G163K, P256T, G91T, G38A, D27R, and N33Q of SEQ ID NO: 2.

In a further embodiment, the lipase is a variant having lipase activity and at least 60% such as at least 65%, at least 70%, at least 75%, at least 80%, at least 85%, at least 90%, at least 95% identity, at least 96%, at least 97%, at least 98%, or at least 99%, but less than 100% sequence identity with SEQ ID NO: 1, and comprises substitutions at positions corresponding to T231R+N233R and at least one or more (e.g., several) of D96E, D111A, D254S, G163K, P256T, G91T, G38A, D27R, and N33Q of SEQ ID NO: 2 selected from the group of:
 a) D96E T231R N233R;
 b) N33Q D96E T231R N233R;
 c) N33Q T231R N233R;
 d) N33Q D111A T231R N233R;
 e) N33Q T231R N233R P256T;
 f) N33Q G38A G91T G163K T231R N233R D254S;
 g) N33Q G38A G91T D96E D111A G163K T231R N233R D254S P256T;

h) D27R N33Q G38A D96E D111A G163K T231R N233R D254S P256T;

i) D27R N33Q G38A G91T D96E D111A G163K T231R N233R P256T;

j) D27R N33Q G38A G91T D96E D111A G163K T231R N233R D254S;

k) D27R G38A G91T D96E D111A G163K T231R N233R D254S P256T;

l) D96E T231R N233R D254S;

m) T231R N233R D254S P256T;

n) G163K T231R N233R D254S;

o) D27R N33Q G38A G91T D96E G163K T231R N233R D254S P256T;

p) D27R G91T D96E D111A G163K T231R N233R D254S P256T;

q) D96E G163K T231R N233R D254S;

r) D27R G163K T231R N233R D254S;

s) D27R G38A G91T D96E D111A G163K T231R N233R D254S;

t) D27R G38A G91T D96E G163K T231R N233R D254S P256T;

u) D27R G38A D96E D111A G163K T231R N233R D254S P256T;

v) D27R D96E G163K T231R N233R D254S;

w) D27R D96E D111A G163K T231R N233R D254S P256T;

x) D27R G38A D96E G163K T231R N233R D254S P256T.

Such useful variants of a parent lipase are provided, e. g. in WO 2015/049370.

Lipase Activity:

In the context of the present invention, the lipolytic activity may be determined as lipase units (LU), using tributyrate as substrate. The method is based on the hydrolysis of tributyrin by the enzyme, and the alkali consumption to keep pH constant during hydrolysis is registered as a function of time

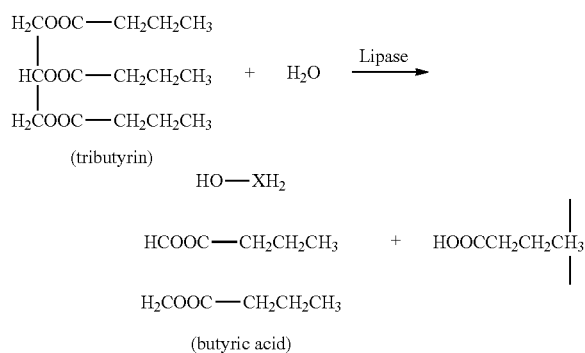

According to the invention, one lipase unit (LU) may be defined as the amount of enzyme which, under standard conditions (i.e. at 30° C.; pH 7.0; with 0.1% (w/v) Gum Arabic as emulsifier and 0.16 M tributyrine as substrate) liberates 1 micromol titrable butyric acid per minute.

Alternatively, lipolytic activity may be determined as Long Chain Lipase Units (LCLU) using substrate pNP-Palmitate (C:16) when incubated at pH 8.0, 30° C., the lipase hydrolyzes the ester bond and releases pNP, which is yellow and can be detected at 405 nm.

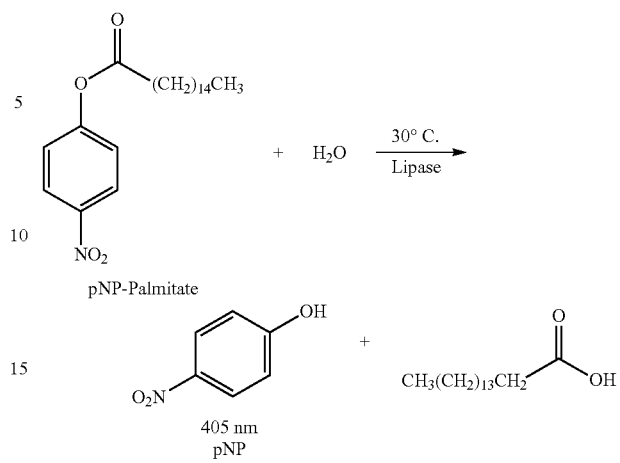

Phospholipases:

The one or more lipolytic enzyme may include a polypeptide having phospholipase activity, preferably phospholipase $A_1$, phospholipase $A_2$, phospholipase B, phospholipase C, phospholipase D, lyso-phospholipases activity, and/or any combination thereof. In the process of the invention the one or more lipolytic enzyme may be a phospholipase, e.g., a single phospholipase such as $A_1$, $A_2$, B, C, or D; two or more phospholipases, e.g., two phospholipases, including, without limitation, both type A and B; both type $A_1$ and $A_2$; both type $A_1$ and B; both type $A_2$ and B; both type $A_1$ and C; both type $A_2$ and C; or two or more different phospholipases of the same type.

The one or more lipolytic enzyme may be a polypeptide having phospholipase activity, as well as having acyltransferase activity, e.g., a polypeptide selected from the polypeptides disclosed in WO 2003/100044, WO 2004/064537, WO 2005/066347, WO 2008/019069, WO 2009/002480, and WO 2009/081094. Acyltransferase activity may be e.g., determined by the assays described in WO 2004/064537.

The phospholipase may be selected from the polypeptides disclosed in WO 2008/036863 and WO 20003/2758. Suitable phospholipase preparations are PURIFINE® (available from Verenium) and LECITASE® ULTRA (available from Novozymes A/S). An enzyme having acyltransferase activity is available as the commercial enzyme preparation LYSOMAX® OIL (available from Danisco A/S).

Cutinases: The one or more lipolytic enzyme may include a polypeptide having cutinase activity.

The cutinase may e.g., be selected from the polypeptides disclosed in WO 2001/92502, in particular the *Humicola insolens* cutinase variants disclosed in Example 2.

Preferably, the one or more lipolytic enzyme is an enzyme having at least 60%, at least 70%, at least 80%, at least 90%, at least 95%, at least 96%, at least 97%, at least 98%, or even at least 99% identity to any of the aforementioned lipases, phospholipases, cutinases, and acyltransferases.

In one embodiment, the one or more lipolytic enzyme has at least 60%, at least 70%, at least 80%, at least 90%, at least 95%, at least 96%, at least 97%, at least 98%, at least or even at least 99% identity to the amino acid sequence shown as positions 1-269 of SEQ ID NO: 2 of WO 95/22615.

Enzyme sources and formulation: The one or more lipolytic enzyme used in the process of the invention may be derived or obtainable from any of the sources mentioned herein. The term "derived" means in this context that the enzyme may have been isolated from an organism where it is present natively, i.e. the identity of the amino acid sequence of the enzyme are identical to a native enzyme. The term "derived" also means that the enzymes may have been produced recombinantly in a host organism, the recombinant produced enzyme having either an identity identical to a native enzyme or having a modified amino acid sequence, e.g., having one or more amino acids which are deleted, inserted and/or substituted, i.e. a recombinantly produced enzyme which is a mutant and/or a fragment of a native amino acid sequence. Within the meaning of a native enzyme are included natural variants. Furthermore, the term "derived" includes enzymes produced synthetically by e.g., peptide synthesis. The term "derived" also encompasses enzymes which have been modified e.g., by glycosylation, phosphorylation etc., whether in vivo or in vitro. The term "obtainable" in this context means that the enzyme has an amino acid sequence identical to a native enzyme. The term encompasses an enzyme that has been isolated from an organism where it is present natively, or one in which it has been expressed recombinantly in the same type of organism or another, or enzymes produced synthetically by e.g., peptide synthesis. With respect to recombinantly produced enzyme the terms "obtainable" and "derived" refers to the identity of the enzyme and not the identity of the host organism in which it is produced recombinantly.

Accordingly, the one or more lipolytic enzyme may be obtained from a microorganism by use of any suitable technique. For instance, an enzyme preparation may be obtained by fermentation of a suitable microorganism and subsequent isolation of an enzyme preparation from the resulting fermented broth or microorganism by methods known in the art. The enzyme may also be obtained by use of recombinant DNA techniques. Such method normally comprises cultivation of a host cell transformed with a recombinant DNA vector comprising a DNA sequence encoding the enzyme in question and the DNA sequence being operationally linked with an appropriate expression signal such that it is capable of expressing the enzyme in a culture medium under conditions permitting the expression of the enzyme and recovering the enzyme from the culture. The DNA sequence may also be incorporated into the genome of the host cell. The DNA sequence may be of genomic, cDNA or synthetic origin or any combinations of these, and may be isolated or synthesized in accordance with methods known in the art.

The one or more lipolytic enzyme may be applied in any suitable formulation, e.g., as lyophilised powder or in aqueous solution.

Sequence Identity

The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSU M62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

Process Design

The present invention provides a process for production of fatty acid alkyl esters, by reacting a fatty acid feedstock with an alcohol in the presence of water and one or more lipolytic enzymes, in a system/reaction system comprising an oil phase/hydrophobic phase and a hydrophilic phase. The reaction of said fatty acid feed stock, including any triglyceride, diglyceride, monoglyceride, free fatty acid or any combination thereof contained in the fatty acid feedstock, with said alcohol produces fatty acid alkyl esters/biodiesel and glycerol. As the reaction proceeds, fatty acid alkyl esters accumulate in the oil phase/hydrophobic phase.

The inventors of the present invention have observed that, in processes where fatty acid alkyl esters/biodiesel is produced by enzymatic bioconversion of a fatty acid feedstock, the salt contamination of the resulting glycerol is unexpectedly low and the glycerol has a sufficiently low content of salt to be readily processed into high quality or technical grade glycerol, such as by neutralization or saphonation, even if caustic treatment is performed without effectively having separated the oil phase/hydrophobic phase from the hydrophilic phase.

Hence, in the process according to the Invention, fatty acid alkyl esters/biodiesel is/are produced under conditions under which separation of the oil phase/hydrophobic phase containing the fatty acid esters/biodiesel form the hydrophilic phase prior to any further processing of the fatty acid esters/biodiesel, such as treatment with an alkaline agent to remove free fatty acids, can be avoided. This provides a number of significant benefits: Firstly, it is possible to design a process for production of fatty acid and eventually refined products, including biodiesel and glycerol, with fewer and less costly process steps and, shorter process time and higher capacity. Also, since phase separation occurs after caustic treatment, it is possible to use elevated temperatures, which enables faster separation of the phases.

The present inventors have also found that after alkaline treatment, the process according to the invention produces a fatty acid alkyl ester/biodiesel phase or composition, which has reduced content of soap or salts of the free fatty acids, which makes subsequent, sequential washing steps less costly.

Finally, the process according to the invention gives a higher yield as very few fatty acid alkyl esters are trapped in soap emulsions and no fatty acid alkyl esters are trapped in enzyme emulsion phases.

In one main aspect of the invention, formation of soap/salt free fatty acids in the oil phase/the hydrophobic phase is achieved by treatment with one or more alkaline agents in the presence of said alcohol/said hydrophobic phase. Hence, the process comprises contacting fatty acid alkyl esters, free fatty acids, water, alcohol and glycerol and one or more lipolytic enzymes with one or more alkaline agents under conditions allowing formation of soap/salts of the free fatty acids.

According to this aspect of the invention is provided a process for production of fatty acid alkyl esters, which comprising i) reacting a fatty acid feedstock with an alcohol in the presence of water and one or more lipolytic enzymes, in a reaction system comprising an oil phase/hydrophobic phase, and a hydrophilic phase to produce fatty acid alkyl esters and glycerol; and j) removing or reducing the amount of free fatty acids by treatment with one or more alkaline agents to form soap/salts of the free fatty acids, prior to separating the oil phase/hydrophobic phase from the hydrophilic phase; i.e. while there is still an oil phase/hydrophobic phase and a hydrophilic phase in said reaction system.

The process according to the invention may further comprise
i) providing a system, such as a reaction system, comprising said oil phase/hydrophobic phase and said hydrophilic phase,
ii) reacting a fatty acid feedstock present in said oil phase/hydrophobic phase with alcohol in the presence of water and one or more lipolytic enzymes to produce said fatty acid alkyl esters, free fatty acids and glycerol.

According to some embodiments, the process comprises separating the soap/salts of said free fatty acids produced in step ii) from the fatty acid esters and the one or more lipolytic enzymes, such as by separating the fatty acid alkyl esters from the hydrophilic phase containing said soap/salts and the one or more lipolytic enzymes.

Accordingly, the invention provides a process for production of fatty acid alkyl esters which comprises
i) providing a system, such as a reaction system, comprising an oil phase/hydrophobic phase and a hydrophilic phase,
ii) reacting a fatty acid feedstock present in said oil phase/hydrophobic phase with alcohol, in the presence of water and one or more lipolytic enzymes, to produce said fatty acid alkyl esters;
iii) reacting free fatty acids in said oil phase/hydrophobic phase with one or more alkaline agents; and
iv) separating said fatty acid alkyl esters from said hydrophilic phase In further embodiments, the process according to the invention, comprises
i) providing a reaction system having an oil phase/hydrophobic phase that comprises a fatty acid feedstock, and a hydrophilic phase that comprises alcohol, water and one or more lipolytic enzymes;
ii) reacting the fatty acid feedstock with the alcohol in the presence of said water and said one or more lipolytic enzymes to produce free fatty acids, glycerol; and fatty acid alkyl esters;
iii) adding one or more alkaline agents to the reaction system to allow formation of soap/salts of the free fatty acids produced in step ii); and
iv) separating the fatty acid alkyl esters from the soap/salts of the fatty acid and the one or more lipolytic enzymes.

The one or more lipolytic enzymes used in the process of the invention may in particular be selected from lipase, phospholipase, cutinase and a mixture thereof.

It is particularly preferred that at least one of the one or more lipolytic enzymes is a lipase, and, optionally, that one or more lipase(s) are used in combination with one or more phospholipases and or one or more cutinases. As the skilled person will understand, the use of phospholipases in combination with other lipolytic enzymes, such as lipases and cutinases, is relevant when the fatty acid feedstock contains impurities in the form of phospholipids. The combined use of one or more lipases and one or more phospholipases results in combined transesterification and reduction of phospholipids (degumming) and hence produces phosphorous reduced fatty acid alkyl esters, Such a process for producing phosphorous reduced fatty acid alkyl esters, comprising mixing an alcohol, a substrate comprising triglyceride and/or fatty acids, with one or more lipolytic enzymes including lipases, cutinases and acyltransferases, and one or more phospholipases and water is disclosed in WO 2006/133698, the content of which is incorporated herein by reference in its entirety.

In order to minimize the amount of enzyme, which is lost in the caustic treatment, the present inventors have also been able to reduce the amounts of enzyme used in the process for production of fatty acid alkyl esters. Hence, the amount of said one or more lipolytic enzymes is preferably within the range of 100 to 500 enzyme units/g oil phase/hydrophobic phase, such as in the range of 100 to 490 enzyme units/g oil phase/hydrophobic phase, 100 to 480 enzyme units/g oil phase/hydrophobic phase, 100 to 475 enzyme units/g oil phase/hydrophobic phase, 100 to 450 enzyme units/g oil phase/hydrophobic phase, 100 to 425 enzyme units/g oil phase/hydrophobic phase, 100 to 400 enzyme units/g oil phase/hydrophobic phase, 100 to 375 enzyme units/g oil phase/hydrophobic phase, 100 to 350 enzyme units/g oil phase/hydrophobic phase, 100 to 325 enzyme units/g oil phase/hydrophobic phase, 100 to 300 enzyme units/g oil phase/hydrophobic phase, 150 to 500 enzyme units/g oil phase/hydrophobic phase, 150 to 490 enzyme units/g oil phase/hydrophobic phase, 150 to 480 enzyme units/g oil phase/hydrophobic phase, 150 to 475 enzyme units/g oil phase/hydrophobic phase, 150 to 450 enzyme units/g oil phase/hydrophobic phase, 150 to 425 enzyme units/g oil phase/hydrophobic phase, 150 to 400 enzyme units/g oil phase/hydrophobic phase, 150 to 375 enzyme units/g oil phase/hydrophobic phase, 150 to 350 enzyme units/g oil phase/hydrophobic phase, 150 to 325 enzyme units/g oil phase/hydrophobic phase, 150 to 300 enzyme units/g oil phase/hydrophobic phase, 200 to 490 enzyme units/g oil phase/hydrophobic phase, 200 to 480 enzyme units/g oil phase/hydrophobic phase, 200 to 475 enzyme units/g oil phase/hydrophobic phase, 200 to 450 enzyme units/g oil phase/hydrophobic phase, 200 to 425 enzyme units/g oil phase/hydrophobic phase, 200 to 400 enzyme units/g oil phase/hydrophobic phase, 200 to 375 enzyme units/g oil phase/hydrophobic phase, 200 to 350 enzyme units/g oil phase/hydrophobic phase, 200 to 325 enzyme units/g oil phase/hydrophobic phase, or such as 200 to 300 enzyme units/g oil phase/hydrophobic phase.

Accordingly, the process of the invention may comprise
i) providing a system comprising an oil phase/hydrophobic phase an a hydrophilic phase, and
ii) reacting a fatty acid feedstock present in said oil phase/hydrophobic phase with alcohol in the presence of water and one or more lipolytic enzymes;
wherein the total amount of said one or more lipolytic enzymes is within the range of 100 to 500 enzyme units/g oil phase/hydrophobic phase, such as in the range of 100 to 490 enzyme units/g oil phase/hydrophobic phase, 100 to 480 enzyme units/g oil phase/hydrophobic phase, 100 to 475 enzyme units/g oil phase/hydrophobic phase, 100 to 450 enzyme units/g oil phase/hydrophobic phase, 100 to 425 enzyme units/g oil phase/hydrophobic phase, 100 to 400 enzyme units/g oil phase/hydrophobic phase, 100 to 375 enzyme units/g oil phase/hydrophobic phase, 100 to 350 enzyme units/g oil phase/hydrophobic phase, 100 to 325 enzyme units/g oil phase/hydrophobic phase, 100 to 300 enzyme units/g oil phase/hydrophobic phase, 150 to 500 enzyme units/g oil phase/hydrophobic phase, 150 to 490 enzyme units/g oil phase/hydrophobic phase, 150 to 480 enzyme units/g oil phase/hydrophobic phase, 150 to 475 enzyme units/g oil phase/hydrophobic phase, 150 to 450 enzyme units/g oil phase/hydrophobic phase, 150 to 425 enzyme units/g oil phase/hydrophobic phase, 150 to 400 enzyme units/g oil phase/hydrophobic phase, 150 to 375 enzyme units/g oil phase/hydrophobic phase, 150 to 350 enzyme units/g oil phase/hydrophobic phase, 150 to 325 enzyme units/g oil phase/hydrophobic phase, 150 to 300 enzyme units/g oil phase/hydrophobic phase, 200 to 490 enzyme units/g oil phase/hydrophobic phase, 200 to 480 enzyme units/g oil phase/hydrophobic phase, 200 to 475 enzyme units/g oil phase/hydrophobic phase, 200 to 450 enzyme units/g oil phase/hydrophobic phase, 200 to 425 enzyme units/g oil phase/hydrophobic phase, 200 to 400 enzyme units/g oil phase/hydrophobic phase, 200 to 375 enzyme units/g oil phase/hydrophobic phase, 200 to 350 enzyme units/g oil phase/hydrophobic phase, 200 to 325 enzyme units/g oil phase/hydrophobic phase, or such as 200 to 300 enzyme units/g oil phase/hydrophobic phase.

According to some embodiments of the invention, wherein the one or more lipolytic enzymes is/are selected from lipases, such as the lipase set forth in SEQ ID NO: 1, it is to be understood that the amount of enzyme is provided in lipase units. Hence, when lipase is preferred, the amount of lipolytic enzyme is preferably within the range of 100 to 500 lipase units/g oil phase/hydrophobic phase, such as in the range of 100 to 490 lipase units/g oil phase/hydrophobic phase, 100 to 480 lipase units/g oil phase/hydrophobic phase, 100 to 475 lipase units/g oil phase/hydrophobic phase, 100 to 450 lipase units/g oil phase/hydrophobic phase, 100 to 425 lipase units/g oil phase/hydrophobic phase, 100 to 400 lipase units/g oil phase/hydrophobic phase, 100 to 375 lipase units/g oil phase/hydrophobic phase, 100 to 350 lipase units/g oil phase/hydrophobic phase, 100 to 325 lipase units/g oil phase/hydrophobic phase, 100 to 300 lipase units/g oil phase/hydrophobic phase, 150 to 500 lipase units/g oil phase/hydrophobic phase, 150 to 490 lipase units/g oil phase/hydrophobic phase, 150 to 480 lipase units/g oil phase/hydrophobic phase, 150 to 475 lipase units/g oil phase/hydrophobic phase, 150 to 450 lipase units/g oil phase/hydrophobic phase, 150 to 425 lipase units/g oil phase/hydrophobic phase, 150 to 400 lipase units/g oil phase/hydrophobic phase, 150 to 375 lipase units/g oil phase/hydrophobic phase, 150 to 350 lipase units/g oil phase/hydrophobic phase, 150 to 325 lipase units/g oil phase/hydrophobic phase, 150 to 300 lipase units/g oil phase/hydrophobic phase, 200 to 490 lipase units/g oil phase/hydrophobic phase, 200 to 480 lipase units/g oil phase/hydrophobic phase, 200 to 475 lipase units/g oil phase/hydrophobic phase, 200 to 450 lipase units/g oil phase/hydrophobic phase, 200 to 425 lipase units/g oil phase/hydrophobic phase, 200 to 400 lipase units/g oil phase/hydrophobic phase, 200 to 375 lipase units/g oil phase/hydrophobic phase, 200 to 350 lipase units/g oil phase/hydrophobic phase, 200 to 325 lipase units/g oil phase/hydrophobic phase, or such as 200 to 300 lipase units/g oil phase/hydrophobic phase.

According to other embodiments of the invention, wherein the one or more lipolytic enzymes is/are selected from lipases, such as the lipase set forth in SEQ ID NO: 2 and subsequences and variants thereof as disclosed herein above, the amount of enzyme is provided in Long Chain Lipase Units (LCLU). In such embodiments, the amount of lipolytic enzyme is preferably within the range of 100 to 500 LCLU/g oil phase/hydrophobic phase, such as in the range of 100 to 490 LCLU/g oil phase/hydrophobic phase, 100 to 480 LCLU/g oil phase/hydrophobic phase, 100 to 475 LCLU/g oil phase/hydrophobic phase, 100 to 450 LCLU/g oil phase/hydrophobic phase, 100 to 425 LCLU/g oil phase/hydrophobic phase, 100 to 400 LCLU/g oil phase/hydrophobic phase, 100 to 375 LCLU/g oil phase/hydrophobic phase, 100 to 350 LCLU/g oil phase/hydrophobic phase, 100 to 325 LCLU/g oil phase/hydrophobic phase, 100 to 300 LCLU/g oil phase/hydrophobic phase, 150 to 500 LCLU/g oil phase/hydrophobic phase, 150 to 490 LCLU/g oil phase/hydrophobic phase, 150 to 480 LCLU/g oil phase/hydrophobic phase, 150 to 475 LCLU/g oil phase/hydrophobic phase, 150 to 450 LCLU/g oil phase/hydrophobic phase, 150 to 425 LCLU/g oil phase/hydrophobic phase, 150 to 400 LCLU/g oil phase/hydrophobic phase, 150 to 375 LCLU/g oil phase/hydrophobic phase, 150 to 350 LCLU/g oil phase/hydrophobic phase, 150 to 325 LCLU/g oil phase/hydrophobic phase, 150 to 300 LCLU/g oil phase/hydrophobic phase, 200 to 490 LCLU/g oil phase/hydrophobic phase, 200 to 480 LCLU/g oil phase/hydrophobic phase, 200 to 475 LCLU/g oil phase/hydrophobic phase, 200 to 450 LCLU/g oil phase/hydrophobic phase, 200 to 425 LCLU/g oil phase/hydrophobic phase, 200 to 400 LCLU/g oil phase/hydrophobic phase, 200 to 375 LCLU/g oil phase/hydrophobic phase, 200 to 350 LCLU/g oil phase/hydrophobic phase, 200 to 325 LCLU/g oil phase/hydrophobic phase, or such as 200 to 300 LCLU/g oil phase/hydrophobic phase.

In other embodiments of the invention, the amount of said one or more lipolytic enzymes is preferably within the range of 0.005-5 g enzyme protein (EP)/kg oil phase/hydrophobic phase or fatty acid feedstock, such as within the range of 0.005-2.5 g EP/kg oil phase/hydrophobic phase or fatty acid feedstock, 0.005-1 g EP/kg oil phase/hydrophobic phase or fatty acid feedstock, 0.005-0.75 g EP/kg oil phase/hydrophobic phase or fatty acid feedstock, 0.005-0.5 g EP/kg oil phase/hydrophobic phase or fatty acid feedstock, 0.005-0.25 g EP/kg oil phase/hydrophobic phase or fatty acid feedstock, 0.005-0.1 g EP/kg oil phase/hydrophobic phase or fatty acid feedstock, 0.005-0.075 g EP/kg oil phase/hydrophobic phase or fatty acid feedstock, 0.005-0.05 g EP/kg oil phase/hydrophobic phase or fatty acid feedstock, 0.005-0.025 g EP/kg oil phase/hydrophobic phase or fatty acid feedstock, 0.005-0.01 g EP/kg oil phase/hydrophobic phase or fatty acid feedstock, 0.01-5 g EP/kg oil phase/hydrophobic phase or fatty acid feedstock, 0.02-5 g EP/kg oil phase/hydrophobic phase or fatty acid feedstock, 0.03-5 g EP/kg oil phase/hydrophobic phase or fatty acid feedstock, 0.04-5 g EP/kg oil phase/hydrophobic phase or fatty acid feedstock, 0.05-5 g EP/kg oil phase/hydrophobic phase or fatty acid feedstock, 0.06-5 g EP/kg oil phase/hydrophobic phase or fatty acid feedstock, 0.07-5 g EP/kg oil phase/hydrophobic phase or fatty acid feedstock, 0.08-5 g EP/kg oil phase/hydrophobic phase or fatty acid feedstock, 0.09-5 g EP/kg oil phase/hydrophobic phase or fatty acid feedstock, 0.1-5 g EP/kg oil phase/hydrophobic phase or fatty acid feedstock, 0.2-5 g EP/kg oil phase/hydrophobic phase or fatty acid feedstock, 0.3-5 g EP/kg oil phase/hydrophobic phase or fatty acid feedstock, 0.4-5 g EP/kg oil phase/hydrophobic phase or fatty acid feedstock, 0.5-5 g EP/kg oil phase/hydrophobic phase or fatty acid feedstock, 0.6-5 g EP/kg oil phase/hydrophobic phase or fatty acid feedstock, 0.7-5 g EP/kg oil phase/hydrophobic phase or fatty acid feedstock, 0.8-5 g EP/kg oil phase/hydrophobic phase or fatty acid feedstock, 0.9-5 g EP/kg oil phase/hydrophobic phase or fatty acid feedstock, 1-5 g EP/kg oil phase/hydrophobic phase or fatty acid feedstock, 2-5 g EP/kg oil phase/hydrophobic phase or fatty acid feedstock, 3-5 g EP/kg oil phase/hydrophobic phase or fatty acid feedstock, 4-5 g EP/kg oil phase/hydrophobic phase or fatty acid feedstock, 0.01-4 g EP/kg oil phase/hydrophobic phase or fatty acid feedstock, 0.02-3 g EP/kg oil phase/hydrophobic phase or fatty acid feedstock, 0.03-2 g EP/kg oil phase/hydrophobic phase or fatty acid feedstock, 0.04-1 g EP/kg oil phase/hydrophobic phase or fatty acid feedstock, 0.05-0.9 g EP/kg oil phase/hydrophobic phase or fatty acid feedstock, 0.06-0.8 g EP/kg oil phase/ hydrophobic phase or fatty acid feedstock, 0.07-0.7 g EP/kg oil phase/hydrophobic phase or fatty acid feedstock, 0.08- 0.6 g EP/kg oil phase/hydrophobic phase or fatty acid feedstock, 0.09-0.5 g EP/kg oil phase/hydrophobic phase or fatty acid feedstock, 0.1-0.4 g EP/kg oil phase/hydrophobic phase or fatty acid feedstock, 0.1-0.3 g EP/kg oil phase/ hydrophobic phase or fatty acid feedstock, or such as within the range of 0.1-0.25 g EP/kg oil phase/hydrophobic phase or fatty acid feedstock.

In some embodiments of the above aspects of the invention, the said fatty acid feedstock or any triglyceride, diglyceride, monoglyceride, free fatty acid or any combination thereof contained therein, is reacted with said alcohol such that the oil phase/hydrophobic phase comprises or essentially consists of fatty acid alkyl esters and free fatty acids.

The process of the invention preferably comprises reacting the fatty acid feed stock with said alcohol until at least 60% (w/w), such as at least 65% (w/w), at least 70% (w/w), at least 75% (w/w), at least 80% (w/w), at least 85% (w/w), at least 90% (w/w) or such as at least 95% (w/w) of the fatty acid acyl groups and/or free fatty acids in said fatty acid feed stock have been converted to fatty acid alkyl esters.

In particular embodiments of the invention, the amount of water corresponds to 0.5 to 5.0% (w/w) of said oil phase/ hydrophobic phase, such as 0.5 to 4.0% (w/w) of said oil phase/hydrophobic phase, 0.5 to 3.75%, 0.5 to 3.5%, 0.5 to 3.25%, 0.5 to 3.0%, 0.5 to 2.75%, 0.5 to 2.5%, 0.5 to 2.25%, 0.5 to 2.0%, 0.5 to 1.9%, 0.5 to 1.8.%, 0.5 to 1.75%, 0.75 to 2.0%, 0.75 to 1.8%, 0.75 to 1.75%, 0.75 to 1.5%, 1.0 to 2.0%, 1.0 to 1.9%, 1.0 to 1.8%, or such as 1.0 to 1.5% (w/w) of said oil phase/hydrophobic phase. As the skilled person will understand, the need to add water separately during the process depends on the amount of water in the fatty acid feedstock.

In further embodiments, the process comprises increasing the amount of glycerol in said hydrophilic phase to 2 to 30% (w/w), preferably from 2 to 20% (w/w), such as from 2 to 20% (w/w) relative to the oil phase/hydrophobic phase, by reaction of fatty acid feedstock and, optionally, by further addition of glycerol.

In still further embodiments, the alcohol is added to reach an amount, which is within the range of 12 to 34% (w/w) relative to the oil phase/hydrophobic phase, such as in the range of 17 to 34% (w/w) relative to the oil phase/hydrophobic phase or such as in the range of 12 to 24% (w/w) relative to the oil phase/hydrophobic phase. When the alcohol is methanol, a range of 12 to 24% (w/w) relative to the oil phase/hydrophobic phase is preferred, while a range of 17 to 34% (w/w) relative to the oil phase/hydrophobic phase is preferred when the alcohol is ethanol.

The fatty acid feedstock may be reacted with said alcohol at a temperature which is within the range of 32 to 45° C., preferably within the range of 32 to 40° C. As the skilled person will understand the upper temperature limit depends on the thermophilicity of the one or more lipolytic enzymes employed in the process.

The process of the invention may comprise reacting said fatty acid feedstock with said alcohol for 16-50 hours, such as for 24-50 hours, such as for 30-50 hours, for 30-45 hours, for 35-50 hours, for 35-45 hours, for 38-42 hours, preferably for 35-40 hours.

As the skilled person will understand, the process of the invention may proceed in a batch mode or in a continuous mode. In a continuous mode process the two phases, the oil phase/hydrophobic phase and the hydrophilic phase, respectively, can be processed counter-currently. Kosugi et al. (1990), Biotechnology and Bioengineering, vol. 36, 617- 622, describes a continuous, counter-current process to hydrolyse vegetable oil by immobilized lipase.

The alcohol used in the process may be a C1-C5 alcohol, preferably ethanol or methanol. Methanol is currently the most preferred.

The said alcohol may be added stepwise and/or continuously. Stepwise addition of the alcohol may be in 1, 2, 3, 4, 5, 6, 7, 8, 9, 10 or more steps.

It is to be understood that at least one of said one or more lipolytic enzymes used in the process of the invention may be a liquid enzyme.

In particular, the one or more lipolytic enzyme may be selected from lipase, phospholipase, cutinase and a mixture thereof.

According to some embodiments, it is preferred that the one or more lipolytic enzymes is/are lipase(s). According to other embodiments, a mixture of lipase and phospholipase is used. This combination may be preferred in particular if degumming of the fatty acid feedstock is required The fatty acid feedstock may in particular be derived from one or more of algae oil, canola oil, coconut oil, castor oil, coconut oil, copra oil, corn oil, distiller's corn oil, corn oil free fatty acid distillate, cottonseed oil, flax oil, fish oil, grape seed oil, hemp oil, jatropha oil, jojoba oil, mustard oil, canola oil, palm oil, palm stearin, palm olein, palm kernel oil, peanut oil, rapeseed oil, rice bran oil, safflower oil, soybean oil, sunflower oil, tall oil, oil from halophytes, and/or animal fat, including tallow from pigs, beef and sheep, lard, chicken fat, fish oil, palm oil free fatty acid distillate, soy oil free fatty acid distillate, soap stock fatty acid material, yellow grease, and brown grease or any combination thereof.

According to other embodiments, the fatty acid feedstock may be oil selected from the group consisting of: algae oil, castor oil, coconut oil (copra oil), corn oil, cottonseed oil, flax oil, fish oil, grape seed oil, hemp oil, jatropha oil, jojoba oil, mustard oil, canola oil, palm oil, palm stearin, palm olein, palm kernel oil, peanut oil, rapeseed oil, rice bran oil, safflower oil, soybean oil, sunflower oil, tall oil, and oil from halophytes, or any combination thereof.

The fatty acid feedstock may be fat selected from the group consisting of: animal fat, including tallow from pigs, beef and sheep, lard, chicken fat, fish oil, or any combination thereof.

The fatty acid feedstock may be crude, refined, bleached, deodorized, degummed, or any combination thereof.

Food quality oils and fats are expensive and therefore waste and by-products from their processing as well as non-food grade oils and fats have become increasingly attractive feedstock for fatty acid alkyl ester. Soap stock is the fraction of oil obtained in an oil refinery by treating the oil with a base to convert free fatty acids to soaps (e.g., sodium soaps). The soap stock usually contains a fraction of glycerides beside the soaps. Acid oil is the by-product from the oil refinery produced by acidification of soap stock to solubilize the soaps. It mainly contains free fatty acids (FFA) and acylglycerols. Distillates like Palm Fatty Acid Distillate (PFAD) is the by-product from oil refining coming from a distillation process used to eliminate free fatty acid from the oil.

The feedstock may be an intermediate product, a waste product or a by-product of oil or fat refining selected from the group consisting of: soap stock; acid oil; fatty acid distillates such as PFAD, soy fatty acid distillate, rapeseed fatty acid distillate, rice bran fatty acid distillate, poultry fat fatty acid distillate, beef tallow fatty acid distillate, etc.;

gums from degumming; by-products from the production of omega-3 fatty acids derivates from fish oil; fat trap grease; yellow grease, and brown grease, free fatty acids like oleic acid; or fractions of oil obtained by physical separations; or any combinations thereof.

In an embodiment, solution phases (i.e. the oil phase/hydrophobic phase and the hydrophilic phases) in the system are mixed using a high sheer mixer or cavitator.

In other embodiments, an alkaline agent or base, such as NaOH and/or KOH, is added to said system prior to addition of said one or more lipolytic enzymes. In particular, said alkaline agent or base is added in amounts corresponding to 200 ppm or less, preferably in amounts within the range of 10-100 ppm. The primary purpose of adding alkaline agent or base at this stage in the process is to neutralize trace amounts of mineral acids in the oil.

In further embodiments, said oil phase/hydrophobic phase comprises fatty acid alkyl esters, free fatty acids and, optionally, unreacted fatty acid feedstock; and said hydrophilic phase comprises glycerol, alcohol, water and the one or more lipolytic enzymes.

In further embodiments, said hydrophilic phase constitutes from 5 to 50%, 10 to 50%, 20 to 50%, 20 to 45%, or even 20 to 40% of the reaction system (reactant mixture) (w/w), and glycerol constitutes 30 to 85% (w/w), 40 to 85% (w/w), 45 to 85% (w/w), 50 to 85% (w/w) or even 60 to 80% (w/w) of the hydrophilic phase.

In other embodiments, glycerol constitutes 30 to 70% (w/w), 35 to 70% (w/w), 40 to 70% (w/w) or even 45 to 70% (w/w) of the hydrophilic phase.

As the process proceeds, the amount of glycerol may increase to above the optimal level in the glycerol-water phase. Therefore, it may be advantageous to separate part of the hydrophilic phase from the oil phase/hydrophobic phase comprising the fatty acid alkyl esters, and reuse the separated part e.g., in the process of the invention. As the skilled person will be aware, a part of the hydrophilic phase can be separated from the fatty phase by a decanter, a coalescer, a cyclone or vortex separator, a settler or by centrifugation for reuse of the enzymes. Reusing the part of the hydrophilic phase provides a further advantage as it will also lead to recirculation of at least part of the lipolytic enzymes. When returning the part of the hydrophilic phase to the reactor, fresh liquid lipase may be added to maintain the lipase activity at the desired level and alcohol (e.g. methanol) may be added.

Hence, in some embodiments, the method according to the invention comprises
  i) removing at least a part of said glycerol/said hydrophilic phase from the system, during the reaction of said fatty acid feedstock with said alcohol or when said reaction has terminated; and
  ii) combining it with additional fatty acid feedstock in a process as defined in any of the preceding claims, wherein the process is the same as or is different from the process from which the glycerol/said hydrophilic phase was removed.

According to some embodiments, 30 to 80% (w/w) of said glycerol/said hydrophilic phase is removed, such as 30 to 70% (w/w), such as 40 to 60% (w/w) or 45 to 55% (w/w) of said glycerol/said hydrophilic phase.

In still further embodiments, the said oil phase/hydrophobic phase and said hydrophilic phase is subject to alkaline treatment so as to form soap/salts of said free fatty acids.

In the process according to the invention, it is preferred that treatment with alkaline agent or base, preferably NaOH or KOH or a mixture thereof, to facilitate the isolation of a soap stock fraction containing FFA occurs with little or no separation of the oil and hydrophilic phase before the treatment. Hence, in these embodiments of the invention, both the oil phase/hydrophobic phase and said hydrophilic phase is subject to alkaline treatment so as to form soap/fatty acid salts of at least a part of the free fatty acids present in the oil phase/hydrophobic phase. This does not exclude, however, that the hydrophilic phase be reduced prior to the treatment with alkaline agent, such as when part of the glycerol/the hydrophilic phase is removed in order to be combined with additional fatty acid feedstock as disclosed above. In particular, the hydrophilic phase may be reduced by 30 to 80% (w/w), such as by 30 to 70% (w/w), such as by 40 to 60% (w/w) or by 45 to 55% (w/w) prior to the treatment with alkaline agent.

The alkaline agent/base may be added as a 1-6N solution in water, such as a 2-9N solution, a 3-9N solution, a 4-9N solution, a 5-9N solution a 6-9N solution, a 7-9N solution, a 8-9N solution, such as a 3-6N solution, a 4-6N solution or a 5-6N solution. In some embodiments, a 6-9N solution is preferred as this introduces very little additional water into the system.

In some embodiments, the amount of said base is in the range of 1.0-2.0 molar equivalents to the amount of free fatty acid, such as in the range of 1.05-1.30 molar equivalents or such as in the range of 1.05-1.25 molar equivalents to the amount of free fatty acid.

The alkaline treatment may be performed at a temperature which is within the range of 35 to 85° C., such as within the range of 35 to 80° C., such as 35 to 75° C., 35 to 70° C., 35 to 60° C., 35 to 50° C., 35 to 45° C., 35 to 40° C., 40 to 80° C., such as 40 to 75° C., 40 to 70° C., 40 to 60° C., 40 to 50° C., 40 to 45° C., 45 to 80° C., such as 45 to 75° C., 45 to 70° C., 45 to 60° C., or such as 45 to 50° C.

Generally, it is advantageous operating at temperatures which are as low as possible and well below the boiling point of the alcohol used, such as at approximately 35 to 45° C. where no or little additional heating is required. Hence, the alkaline treatment is preferably performed at a temperature which is within the range of 35 to 45° C., such as within the range of 36 to 45° C., such as 37 to 45° C., 38 to 45° C., 39 to 45° C. or within the range of 40 to 45° C., The skilled person will understand that the upper temperature limit is mainly defined by the boiling point of the alcohol and further depends on the amount of alcohol present in the system and on the efficiency of the scrubber systems installed at the production plant.

The duration of said alkaline treatment may be from 5 minutes to 2 hours, such as from 7 minutes to 2 hours, 10 minutes to 2 hours, 15 minutes to 2 hours, 30 minutes to 2 hours, such as from 30 minutes to 1.5 hours or such as from 30 minutes to 1 hour. In particular, the skilled short duration, e.g. a few minutes, is possible when operating a continuous system.

In further embodiments of the invention, the said alkaline agent/base is added as a non-aqueous solution. In particular, the alkaline agent/base is solubilized in alcohol, such as methanol.

According to other embodiments, the said alkaline agent is sodium methoxide or potassium methoxide or a mixture of the two.

The process according to the invention may further comprise a step, wherein said fatty acid alkyl esters are separated from said soap/fatty acid salts. Separation of fatty acid alkyl esters from the soap/fatty acid salts, when performed in a process according to the present invention is particularly effective. This is mainly because separation of the oil phase/hydrophobic phase, containing the fatty acid esters/biodiesel, from the hydrophilic phase prior to any further processing of the fatty acid esters/biodiesel, such as treatment with an alkaline agent to remove free fatty acids, may be avoided. As a result, the separation of alkyl ester phase from glycerol/soap phase is fast and there is no or little formation of a third, enzyme emulsion phase containing fatty acid esters/biodiesel, glycerol and enzyme and little loss of product (fatty acid esters/biodiesel) in the process.

According to some embodiments of the invention, a further advantage is provided by using a large amount or volume of glycerol, which is effective in extracting soap/fatty acid salts from the fatty acid esters/biodiesel.

The fatty acid alkyl esters may be separated from said soap/fatty acid salts by gravity settling, decanting and/or centrifugation.

In some embodiments of the invention, the treatment with said one or more alkaline agents is performed under conditions and using an amount of alkaline agent, which allow the amounts of said free fatty acids in the oil phase/hydrophobic phase to be reduced to less than 2% (w/w), such as less than 1.5% (w/w), less than 1% (w/w), less than 0.75% (w/w), less than 0.5% (w/w), or such as less than 0.25% (w/w).

According to further embodiments of the invention, the process comprises separating a composition comprising fatty acyl esters from said soap/fatty acyl salts, wherein the content of free fatty acids in said composition is below 2% (w/w), such as below 1.5% (w/w), below 1% (w/w), below 0.75% (w/w), below 0.5% (w/w), or such as below 0.25% (w/w) and/or the content of glycerides (preferably expressed as "bound glycerin"; i.e. glycerol bound in glycerides). in said composition is below 2% (w/w), such as below 1.5% (w/w), below 1% (w/w), below 0.75% (w/w), below 0.5% (w/w), or such as below 0.23% (w/w).

Preferably, the process comprises separating a composition comprising fatty acyl esters from said soap/fatty acyl salts, wherein the content of free fatty acids in said composition is below 0.25% (w/w) and/or the content of glycerides (preferably expressed as "bound glycerin"; i.e. glycerol bound in glycerides) in said composition is below 0.23% (w/w). Hence, according to these embodiments the product of the invention is preferably one that fulfills the specified requirements for biodiesel without need for further refining.

In further embodiments, the process according to the invention comprises separating the oil phase/hydrophobic phase from hydrophilic phase to provide a composition comprising at least 90% (w/w) fatty acid alkyl esters, from 300 to 400 ppm soap, less than 0.25% (w/w) free fatty acids and less than 0.23% (w/w) glycerides (preferably expressed as "bound glycerin"; i.e. glycerol bound in glycerides).

The said soap/fatty acid salts may be subject to acidification to produce free fatty acids, such as by contacting the soap/fatty acid salts with HCl, $H_3PO_4$ and/or $H_2SO_4$. Currently, $H_2SO_4$ and possibly also $H_3PO_4$ are preferred because the resulting salts precipitate easily, and hence may easily be separated from the glycerol to provide a valuable high grade/tech grade glycerol product. A schematic outline of the process according to the invention, which comprises production of tech grade glycerol is illustrated in FIG. 1.

As the skilled person will understand, the free fatty acids produced by acidification of said soap/fatty acid salts may be used as fatty acid feedstock in a process according to the invention as disclosed above.

The amount of free fatty acids produced by acidification of said soap/fatty acid salts may be within the range of 0.5 to 3% (w/w) of the said feedstock, such as from 1 to 2% (w/w) of the said feedstock.

In particular embodiments, the process according to any of the invention comprises the steps of
  i) providing a reaction system comprising an oil phase/hydrophobic phase and a hydrophilic phase; e.g. a reaction system, wherein the oil phase/hydrophobic phase comprises a fatty acid feedstock containing free and/or glyceride bound fatty acids, and the hydrophilic phase comprises water, one or more lipolytic enzymes, and optionally glycerol;
  ii) adding alcohol, such as a C1-C5 alcohol, preferably ethanol or methanol, to said reaction system either step-wise or continuously, to reach an amount, which is within the range of 14 to 24% (w/w) relative to the oil phase/hydrophobic phase;
  iii) subjecting the fatty acid feedstock and the one or more lipolytic enzymes to conditions allowing transesterification of said free and/or glyceride bound fatty acids to provide a composition comprising fatty acid alkyl esters;
  iv) contacting said composition with an alkaline agent/base under conditions allowing formation of fatty acid salts/soap from residual free fatty acids in the composition; and
  v) separating the fatty acid alkyl esters from the fatty acid salts/soap.

In further embodiments, the process according to the invention comprises
  i) providing a system comprising said oil phase/hydrophobic phase and said hydrophilic phase,
  ii) reacting a fatty acid feedstock present in said oil phase/hydrophobic phase with alcohol in the presence of water and one or more lipolytic enzymes to produce said fatty acid alkyl esters and said free fatty acids.
  iii) subjecting the oil phase/hydrophobic phase and the hydrophilic phase to alkaline treatment so as to form soap/fatty acid salts of free fatty acids present in the oil phase/hydrophobic phase
  iv) separating the fatty acid alkyl esters from the hydrophilic phase containing said soap/fatty acid salts
  v) subjecting said hydrophilic phase to acidification, e.g. by addition of $H_2SO_4$ or $H_3PO_4$.

In particular, the said soap/fatty acid salts may be neutralized/subject to acidification, e.g. by addition of $H_2SO_4$ or $H_3PO_4$, so as to form salt, such as $Na_2SO_4$ or $K_2SO_4$, which precipitates in the glycerol.

In a further step, the process preferably comprises separating the precipitated salt from the glycerol, e.g. by filtration.

In order to provide high-grade or tech-grade glycerol the process may further comprise drying said glycerol so as to remove e.g. water and alcohol, such as methanol, from the glycerol.

In particular, the glycerol may be purified, such as by drying and/or removal of alcohol, and or by filtration to produce a composition, wherein the content of glycerol is above 95% (w/w), such as above 97% (w/w), above 97.5% (w/w), above 98% (w/w), above 98.5% (w/w), above 99% (w/w), above 99.5% (w/w), above 99.75% (w/w), above 99.8% (w/w) or is above 99.9% (w/w).

Further, according to these embodiments, the said fatty acid feedstock may be reacted with alcohol in the presence of an amount of glycerol corresponding to 2 to 30% (w/w) or 10 to 12% (w/w) relative to the oil phase/hydrophobic phase, an amount of water corresponding to 1.5 to 5.0% (w/w), or 1.5 to 2.0% (w/w) relative to the oil phase/hydrophobic phase and an amount of alcohol, such as methanol, which is within the range of 14 to 24% (w/w) relative to the oil phase/hydrophobic phase.

The alcohol may be added over a period of 1 to 30 hours, such as over a period of 1 to 20 hours, e.g. a period of 16 hours.

In certain particular embodiments, the said fatty acid feedstock comprises or consists essentially of corn oil or distiller's corn oil.

In a further aspect the present invention provides a process for the manufacture of fatty acid alkyl esters, comprising contacting a fatty acid feedstock with a lipolytic enzymes; the lipolytic enzyme being selected from the group consisting of (a) a polypeptide comprising or consisting of the amino acid sequence set forth in SEQ ID NO: 2;
(b) a polypeptide which is a subsequence of the amino acid sequence set forth in 2;
(c) a polypeptide having at least 60% sequence identity, such as e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, to any of the polypeptides defined in (a) and (b).

The lipase set forth in item (c) may have an amino acid sequence which differs by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 from the polypeptide of SEQ ID NO: 2.

The lipase may be a variant of a parent lipase, which variant has lipase activity and has at least 60%, such at least 65%, at least 70%, at least 75%, at least 80%, at least 85%, at least 90%, at least 95% identity, at least 96%, at least 97%, at least 98%, or at least 99%, but less than 100% sequence identity with SEQ ID NO: 1, and comprises substitutions at positions corresponding to T231R+N233R and at least one or more (e.g., several) of D96E, D111A, D254S, G163K, P256T, G91T, G38A, D27R, and N33Q of SEQ ID NO: 2.

In a further embodiment, the lipase is a variant having lipase activity and at least 60% such at least 65%, at least 70%, at least 75%, at least 80%, at least 85%, at least 90%, at least 95% identity, at least 96%, at least 97%, at least 98%, or at least 99%, but less than 100% sequence identity with SEQ ID NO: 1, and comprises substitutions at positions corresponding to T231R+N233R and at least one or more (e.g., several) of D96E, D111A, D254S, G163K, P256T, G91T, G38A, D27R, and N33Q of SEQ ID NO: 2 selected from the group of:
a) D96E T231R N233R;
b) N33Q D96E T231R N233R;
c) N33Q T231R N233R;
d) N33Q D111A T231R N233R;
e) N33Q T231R N233R P256T;
f) N33Q G38A G91T G163K T231R N233R D254S;
g) N33Q G38A G91T D96E D111A G163K T231R N233R D254S P256T;
h) D27R N33Q G38A D96E D111A G163K T231R N233R D254S P256T;
i) D27R N33Q G38A G91T D96E D111A G163K T231R N233R P256T;
j) D27R N33Q G38A G91T D96E D111A G163K T231R N233R D254S;
k) D27R G38A G91T D96E D111A G163K T231R N233R D254S P256T;
l) D96E T231R N233R D254S;
m) T231R N233R D254S P256T;
n) G163K T231R N233R D254S;
o) D27R N33Q G38A G91T D96E G163K T231R N233R D254S P256T;
p) D27R G91T D96E D111A G163K T231R N233R D254S P256T;
q) D96E G163K T231R N233R D254S;
r) D27R G163K T231R N233R D254S;
s) D27R G38A G91T D96E D111A G163K T231R N233R D254S;
t) D27R G38A G91T D96E G163K T231R N233R D254S P256T;
u) D27R G38A D96E D111A G163K T231R N233R D254S P256T:
v) D27R D96E G163K T231R N233R D254S;
w) D27R D96E D111A G163K T231R N233R D254S P256T;
x) D27R G38A D96E G163K T231R N233R D254S P256T.

In particular embodiments, the process comprises contacting said fatty acid feedstock with an amount of lipase, which is preferably within the range of 0.005-5 g enzyme protein (EP)/kg fatty acid feedstock, such as within the range of 0.005-2.5 g EP/kg fatty acid feedstock, 0.005-1 g EP/kg fatty acid feedstock, 0.005-0.75 g EP/kg fatty acid feedstock, 0.005-0.5 g EP/kg fatty acid feedstock, 0.005-0.25 g EP/kg fatty acid feedstock, 0.005-0.1 g EP/kg fatty acid feedstock, 0.005-0.075 g EP/kg fatty acid feedstock, 0.005-0.05 g EP/kg fatty acid feedstock, 0.005-0.025 g EP/kg fatty acid feedstock, 0.005-0.01 g EP/kg fatty acid feedstock, 0.01-5 g EP/kg fatty acid feedstock, 0.02-5 g EP/kg fatty acid feedstock, 0.03-5 g EP/kg fatty acid feedstock, 0.04-5 g EP/kg fatty acid feedstock, 0.05-5 g EP/kg fatty acid feedstock, 0.06-5 g EP/kg fatty acid feedstock, 0.07-5 g EP/kg fatty acid feedstock, 0.08-5 g EP/kg fatty acid feedstock, 0.09-5 g EP/kg fatty acid feedstock, 0.1-5 g EP/kg fatty acid feedstock, 0.2-5 g EP/kg fatty acid feedstock, 0.3-5 g EP/kg fatty acid feedstock, 0.4-5 g EP/kg fatty acid feedstock, 0.5-5 g EP/kg fatty acid feedstock, 0.6-5 g EP/kg fatty acid feedstock, 0.7-5 g EP/kg fatty acid feedstock, 0.8-5 g EP/kg fatty acid feedstock, 0.9-5 g EP/kg fatty acid feedstock, 1-5 g EP/kg fatty acid feedstock, 2-5 g EP/kg fatty acid feedstock, 3-5 g EP/kg fatty acid feedstock, 4-5 g EP/kg fatty acid feedstock, 0.01-4 g EP/kg fatty acid feedstock, 0.02-3 g EP/kg fatty acid feedstock, 0.03-2 g EP/kg fatty acid feedstock, 0.04-1 g EP/kg fatty acid feedstock, 0.05-0.9 g EP/kg fatty acid feedstock, 0.06-0.8 g EP/kg fatty acid feedstock, 0.07-0.7 g EP/kg fatty acid feedstock, 0.08-0.6 g EP/kg fatty acid feedstock, 0.09-0.5 g EP/kg fatty acid feedstock, 0.1-0.4 g EP/kg fatty acid feedstock, 0.1-0.3 g EP/kg fatty acid feedstock, or such as within the range of 0.1-0.25 g EP/kg fatty acid feedstock.

Fatty Acid Alkyl Ester Composition and its Uses

Fatty acid alkyl esters are used in an extensive range of products and as synthetic intermediates. Some of their industrial applications include use as lubricants, plasticizers, antirust agents, drilling and cutting oils, and starting materials for synthesis of superamides and fatty alcohols. Certain embodiments of the present invention in particular relates to fuels. Fatty acid alkyl esters of short-chain alcohols are non-toxic, biodegradable and an excellent replacement wholly or partly for petroleum based fuel due to the similarity in cetane number, energy content, viscosity and phase changes to those of petroleum based fuels.

Another aspect of the invention pertains to a composition comprising at least 90% (w/w) fatty acid alkyl esters, from 300 to 400 ppm soap, less than 0.25% (w/w) free fatty acids and less than 0.23% (w/w) glycerides, preferably expressed as "bound glycerin"; i.e. glycerol bound in glycerides. With respect to free fatty acids and glycerides, this product meets the specification requirements for biodiesel. Such specification requirements are provided for instance by ASTM International (specification for biodiesel (B100)—ASTM 6751) (available at http://www.astm.org/Standards/). The content of soap is 5-10× lower compared with the soap content in products from previously known processes; it can easily be removed or reduced to acceptable levels by filtration. In particular, the said, said composition may be one which is obtainable by the process disclosed above.

In some embodiments, the composition according to the invention is obtainable by a process, wherein said fatty acid feedstock comprises or consists essentially of corn oil and the said alkaline agent is KOH. The inventors have surprisingly found that when using corn oil as feedstock the process provides a product which typically does not need further processing or purification and is virtually colorless.

Otherwise, the composition according to the invention may potentially be refined or purified by methods known in the art such as distillation (including flash evaporation, stripping, and deodorization); phase separation; extraction; and drying. The purpose of such refining could be to remove or recover one or more of the above mentioned components from the composition. Examples include, but are not limited to, drying for the removal of water. Hence, the crude reactant mixture (composition) can be applied without further refining, or refined by one or more methods.

A further aspect of the invention provides a composition comprising glycerol, said composition being obtainable by the process according to the invention, wherein said soap/fatty acid salts are subject to acidification by contacting the soap/fatty acid salts with $H_3PO_4$ and/or $H_2SO_4$, to produce free fatty acids and salt such as $Na_2SO_4$ or $K_2SO_4$. As mentioned above, acidification of the soap/fatty acid salts with these acids leads to formation of salts which easily precipitate, and may easily be separated from the glycerol to provide a valuable high grade/tech grade glycerol product. As illustrated in FIG. 1 the process for preparation of high grade/tech grade ethanol the said salts may be removed by filtration or otherwise. The process may further comprise drying and/or reducing the amount of alcohol, such as methanol, in said glycerol. The composition obtainable according to the invention may have a glycerol content, which is above 97% (w/w), such as above 97.5% (w/w), above 98% (w/w), above 98.5% (w/w), above 99% (w/w), above 99.5% (w/w), above 99.75% (w/w), above 99.8% (w/w) or is above 99.9% (w/w).

Items

The invention is further disclosed in and defined by any of the following items:

1. A process for production of fatty acid alkyl esters by reacting a fatty acid feedstock with an alcohol in the presence of one or more lipolytic enzymes, in a system comprising an oil phase/hydrophobic phase and a hydrophilic phase, to produce fatty acid alkyl esters and glycerol, wherein soap/salts are formed from residual free fatty acids in the oil phase/hydrophobic phase by treatment with one or more alkaline agents, in the presence of said alcohol/said hydrophobic phase.

2. A process for production of fatty acid alkyl esters comprising reacting a fatty acid feedstock with an alcohol in the presence of water and one or more lipolytic enzymes, in a reaction system comprising an oil phase (hydrophobic phase, and a hydrophilic phase to produce fatty acid alkyl esters and glycerol; and removing or reducing the amount of free fatty acids by treatment with one or more alkaline agents to form soap/salts of the free fatty acids, prior to separating the oil phase (hydrophobic phase from the hydrophilic phase.

3. The process according to item 1 or 2, comprising
   i) providing a system comprising said oil phase/hydrophobic phase and said hydrophilic phase,
   ii) reacting a fatty acid feedstock present in said oil phase/hydrophobic phase with alcohol in the presence of water and one or more lipolytic enzymes to produce said fatty acid alkyl esters, free fatty acids and glycerol.

4. The process according to any of the preceding items, comprising separating the fatty acid alkyl esters from the hydrophilic phase containing said soap/salts and the one or more lipolytic enzymes.

5. The process according to any of the preceding items, wherein the one or more lipolytic enzymes is/are selected from lipase, phospholipase, cutinase and a mixture thereof.

6. The process according to any of the preceding items, comprising
   i) providing a reaction system having an oil phase/hydrophobic phase that comprises a fatty acid feedstock, and a hydrophilic phase that comprises alcohol, water and one or more lipolytic enzymes;
   ii) reacting the fatty acid feedstock with the alcohol in the presence of said water and said one or more lipolytic enzymes to produce free fatty acids, glycerol; and fatty acid alkyl esters;
   iii) adding one or more alkaline agents to the reaction system to allow formation of soap/salts of the free fatty acids produced in step ii); and
   iv) separating the fatty acid alkyl esters from the soap/salts of the fatty acid and the one or more lipolytic enzymes.

7. The process according to any of the preceding items, wherein the one or more lipolytic enzymes is/are lipase(s), optionally in combination with one or more phospholipases and/or one or more cutinases.

8. The process according to any of the preceding items, wherein the total amount of said one or more lipolytic enzymes is within the range of 0.005-5 g enzyme protein (EP)/kg oil phase/hydrophobic phase or fatty acid feedstock, such as within the range of 0.005-2.5 g EP/kg oil phase/hydrophobic phase or fatty acid feedstock, 0.005-1 g EP/kg oil phase/hydrophobic phase or fatty acid feedstock, 0.005-0.75 g EP/kg oil phase/hydrophobic phase or fatty acid feedstock, 0.005-0.5 g EP/kg oil phase/hydrophobic phase or fatty acid feedstock, 0.005-0.25 g EP/kg oil phase/hydrophobic phase or fatty acid feedstock, 0.005-0.1 g EP/kg oil phase/hydrophobic phase or fatty acid feedstock, 0.005-0.075 g EP/kg oil phase/hydrophobic phase or fatty acid feedstock, 0.005-0.05 g EP/kg oil phase/hydrophobic phase or fatty acid feedstock, 0.005-0.025 g EP/kg oil phase/hydrophobic phase or fatty acid feedstock, 0.005-0.01 g EP/kg oil phase/hydrophobic phase or fatty acid feedstock, 0.01-5 g EP/kg oil phase/hydrophobic phase or fatty acid feedstock, 0.02-5 g EP/kg oil phase/hydrophobic phase or fatty acid feedstock, 0.03-5 g EP/kg oil phase/hydrophobic phase or fatty acid feedstock, 0.04-5 g EP/kg oil phase/hydrophobic phase or fatty acid feedstock, 0.05-5 g EP/kg oil phase/hydrophobic phase or fatty acid feedstock, 0.06-5 g EP/kg oil phase/hydrophobic phase or fatty acid feedstock, 0.07-5 g EP/kg oil phase/hydrophobic phase or fatty acid feedstock, 0.08-5 g EP/kg oil phase/hydrophobic phase or fatty acid feedstock, 0.09-5 g EP/kg oil phase/hydrophobic phase or fatty acid feedstock, 0.1-5 g EP/kg oil phase/hydrophobic phase or fatty acid feedstock, 0.2-5 g EP/kg oil phase/hydrophobic phase or fatty acid feedstock, 0.3-5 g EP/kg oil phase/hydrophobic phase or fatty acid feedstock, 0.4-5 g EP/kg oil phase/hydrophobic phase or fatty acid feedstock, 0.5-5 g EP/kg oil phase/hydrophobic phase or fatty acid feedstock, 0.6-5 g EP/kg oil phase/hydrophobic phase or fatty acid feedstock, 0.7-5 g EP/kg oil phase/hydrophobic phase or fatty acid feedstock, 0.8-5 g EP/kg oil phase/hydrophobic phase or fatty acid feedstock, 0.9-5 g EP/kg oil phase/hydrophobic phase or fatty acid feedstock, 1-5 g EP/kg oil phase/hydrophobic phase or fatty acid feedstock, 2-5 g EP/kg oil phase/hydrophobic phase or fatty acid feedstock, 3-5 g EP/kg oil phase/hydrophobic phase or fatty acid feedstock, 4-5 g EP/kg oil phase/hydrophobic phase or fatty acid feedstock, 0.01-4 g EP/kg oil phase/hydrophobic phase or fatty acid feedstock, 0.02-3 g EP/kg oil phase/hydrophobic phase or fatty acid feedstock, 0.03-2 g EP/kg oil phase/hydrophobic phase or fatty acid feedstock, 0.04-1 g EP/kg oil phase/hydrophobic phase or fatty acid feedstock, 0.05-0.9 g EP/kg oil phase/hydrophobic phase or fatty acid feedstock, 0.06-0.8 g EP/kg oil phase/hydrophobic phase or fatty acid feedstock, 0.07-0.7 g EP/kg oil phase/hydrophobic phase or fatty acid feedstock, 0.08-0.6 g EP/kg oil phase/hydrophobic phase or fatty acid feedstock, 0.09-0.5 g EP/kg oil phase/hydrophobic phase or fatty acid feedstock, 0.1-0.4 g EP/kg oil phase/hydrophobic phase or fatty acid feedstock, 0.1-0.3 g EP/kg oil phase/hydrophobic phase or fatty acid feedstock, or such as within the range of 0.1-0.25 g EP/kg oil phase/hydrophobic phase or fatty acid feedstock.

9. The process according to any of the preceding items, wherein step ii) comprises reacting the fatty acid feed stock with said alcohol until at least 60% (w/w), such as at least 65% (w/w), at least 70% (w/w), at least 75% (w/w), at least 80% (w/w), at least 85% (w/w), at least 90% (w/w) or such as at least 95% (w/w) of the fatty acid acyl groups or free fatty acids in said fatty acid feed stock have been converted to fatty acid alkyl esters. 10. The process according to any of the preceding items, wherein the amount of water corresponds to 0.5 to 5.0% (w/w) of said oil phase/hydrophobic phase, such as 0.5 to 4.0% (w/w) of said oil phase/hydrophobic phase, 0.5 to 3.0% (w/w) of said oil phase/hydrophobic phase, 0.5 to 2.5% (w/w) of said oil phase/hydrophobic phase or such as 0.5 to 2.0% (w/w) of said oil phase/hydrophobic phase.

11. The process according to any of the preceding items, comprising increasing the amount of glycerol in said hydrophilic phase to 2 to 30% (w/w), preferably from 2 to 20% (w/w), such as from 2 to 20% (w/w) relative to the oil phase/hydrophobic phase, by reaction of fatty acid feedstock and, optionally, by further addition of glycerol.

12. The process according to any of the preceding items, wherein the alcohol is added to reach an amount, which is within the range of 12 to 34% (w/w) relative to the oil phase/hydrophobic phase, such as in the range of 17 to 34% (w/w) relative to the oil phase/hydrophobic phase or such as in the range of 12 to 24% (w/w) relative to the oil phase/hydrophobic phase.

13. The process according to any of the preceding items, wherein the fatty acid feedstock is reacted with said alcohol at a temperature which is within the range of 32 to 45° C., preferably within the range of 32 to 40° C.

14. The process according to any of the preceding items, comprising reacting said fatty acid feedstock with said alcohol for 16-50 hours, such as for 24-50 hours, such as for 30-50 hours, for 30-45 hours, for 35-50 hours, for 35-45 hours, for 38-42 hours, preferably for 35-40 hours.

15. The process according to any of the preceding items, wherein said process proceeds in a batch mode or in a continuous mode.

16. The process according to any of the preceding items, wherein said alcohol is a C1-C5 alcohol, preferably ethanol or methanol.

17. The process according to any of the preceding items, wherein said alcohol is added stepwise or continuously.

18. The process according to any of the preceding items, wherein at least one of said one or more lipolytic enzymes is a liquid enzyme.

19. The process according to any of the preceding items, wherein the fatty acid feedstock is derived from one or more of algae oil, canola oil, coconut oil, castor oil, coconut oil, copra oil, corn oil, distiller's corn oil, cottonseed oil, flax oil, fish oil, grape seed oil, hemp oil, jatropha oil, jojoba oil, mustard oil, canola oil, palm oil, palm stearin, palm olein, palm kernel oil, peanut oil, rapeseed oil, rice bran oil, safflower oil, soybean oil, sunflower oil, tall oil, oil from halophytes, and/or animal fat, including tallow from pigs, beef and sheep, lard, chicken fat, fish oil, palm oil free fatty acid distillate, soy oil free fatty acid distillate, soap stock fatty acid material, yellow grease, and brown grease or any combination thereof.

20. The process according to any of the preceding items, wherein solution phases in the system/reaction system are mixed using a high shear mixer or cavitator.

21. The process according to any of the preceding items, wherein an alkaline agent or base, such as NaOH and/or KOH, is added to said system prior to addition of said one or more lipolytic enzymes.

22. The process according to item 21, wherein said alkaline agent or base is added in amounts corresponding to 200 ppm or less, preferably in amounts within the range of 10-100 ppm.

23. The method according to any of the preceding items, wherein
said oil phase/hydrophobic phase comprises fatty acid alkyl esters, free fatty acids and, optionally, unreacted fatty acid feedstock; and
said hydrophilic phase comprises glycerol, alcohol, water and the one or more lipolytic enzymes.

24. The process according to any of the preceding items, wherein
said hydrophilic phase constitutes from 5 to 50%, 10 to 50%, 20 to 50%, 20 to 45%, or even 20 to 40% of the system/reaction system (w/w), and
glycerol constitutes 30 to 85% (w/w), 40 to 85% (w/w), 45 to 85% (w/w), 50 to 85% (w/w) or even 60 to 80% (w/w) of the hydrophilic phase.

25. The process according to any of the preceding items, wherein glycerol constitutes 30 to 80% (w/w), 30 to 70% (w/w), 35 to 70% (w/w), 40 to 70% (w/w) or even 45 to 70% (w/w) of the hydrophilic phase.

26. The method according to any of the preceding items, comprising
i) removing at least a part of said glycerol/said hydrophilic phase from the system/reaction system, during the reaction of said fatty acid feedstock with said alcohol or when said reaction has terminated; and
ii) combining it with additional fatty acid feedstock in a process as defined in any of the preceding items, wherein the process is the same as or is different from the process from which the glycerol/said hydrophilic phase was removed.

27. The process according to item 26, wherein 30 to 70% (w/w) of said glycerol/said hydrophilic phase is removed, such as 40 to 60% (w/w) or 45 to 55% (w/w) of said glycerol/said hydrophilic phase.

28. The process according to any of the preceding items, wherein said oil phase/hydrophobic phase and said hydrophilic phase is subject to alkaline treatment so as to form soap/salts of said free fatty acids.

29. The process according to any of the preceding items, wherein the oil phase/hydrophobic phase and said hydrophilic phase is subject to alkaline treatment so as to form soap/fatty acid salts of at least a part of the free fatty acids present in the oil phase/hydrophobic phase.

30. The process according to any of items 28 to 29, wherein said alkaline treatment comprises contacting the oil phase/hydrophobic phase and said hydrophilic phase with an alkaline agent or base selected from KOH. or NaOH or a mixture thereof.

31. The process according to any of items 28 to 30, wherein said alkaline agent/base is added as a 1-6N solution in water, such as a 2-9N solution, a 3-9N solution, a 4-9N solution, a 5-9N solution a 6-9N solution, a 7-9N solution, a 8-9N solution, such as a 3-6N solution, a 4-6N solution or a 5-6N solution.

32. The process according to any of items 28 to 31, wherein the amount of said base is in the range of 1.0-2.0 molar equivalents to the amount of free fatty acid, such as in the range of 1.05-1.30 molar equivalents or such as in the range of 1.05-1.25 molar equivalents to the amount of free fatty acid.

33. The process according to any of items 28 to 32, wherein said alkaline treatment is performed at a temperature which is within the range of 35 to 85° C., such as within the range of 35 to 80° C.

34. The process according to any of items 28 to 33, wherein the duration of said alkaline treatment is from 30 seconds to 2 hours, such as from 30 seconds to 1 hour, from 30 seconds to 30 minutes, from 1 to 30 minutes, from 2-30 minutes, from 3-30 minutes, from 5 minutes to 2 hours, such as from 7 minutes to 2 hours, 10 minutes to 2 hours, 15 minutes to 2 hours, 30 minutes to 2 hours, such as from 30 minutes to 1.5 hours or such as from 30 minutes to 1 hour.

35. The process according to any of items 28 to 34, wherein said alkaline agent/base is added as a non-aqueous solution.

36. The process according to any of items 28-35, wherein said alkaline agent/base is solubilized in alcohol, such as methanol.

37. The process according to any of items 28 to 34, wherein said alkaline agent is sodium methoxide or potassium methoxide or a mixture of the two.

38. The process according to any of items 28-37, wherein said fatty acid alkyl esters are separated from said soap/fatty acid salts.

39. The process according to any of items 28 to 38, wherein said fatty acid alkyl esters are separated from said soap/fatty acid salts by gravity settling, decanting and/or centrifugation.

40. The process according to any of items 28-39, wherein said treatment with one or more alkaline agents is performed under conditions and using an amount of alkaline agent, which allow the amounts of said free fatty acids in the oil phase/hydrophobic phase to be reduced to less than 2% (w/w), such as less than 1.5% (w/w), less than 1% (w/w), less than 0.75% (w/w), less than 0.5% (w/w), or such as less than 0.25% (w/w). 41. The process according to any of items 28 to 39, comprising separating a composition comprising fatty acyl esters from said soap/fatty acyl salts, wherein the content of free fatty acids in said composition is below 0.25% (w/w) and/or the content of glycerides in said composition is below 0.23% (w/w).

42. The process according to any of the preceding items, comprising separating a composition comprising fatty acyl esters from said soap/fatty acyl salts, wherein the content of free fatty acids in said composition is below 2% (w/w), such as below 1.5% (w/w), below 1% (w/w), below 0.75% (w/w), below 0.5% (w/w), or such as below 0.25% (w/w) and/or the content of glycerides (preferably expressed as "bound glycerin"; i.e. glycerol bound in glycerides) in said composition is below 2% (w/w), such as below 1.5% (w/w), below 1% (w/w), below 0.75% (w/w), below 0.5% (w/w), or such as below 0.23% (w/w).

43. The process according to any of the preceding items, comprising separating a composition comprising fatty acyl esters from said soap/fatty acyl salts, wherein the content of free fatty acids in said composition is below 0.25% (w/w) and/or the content of glycerides (preferably expressed as "bound glycerin"; i.e. glycerol bound in glycerides) in said composition is below 0.23% (w/w). Hence, according to these embodiments the product of the invention is preferably one that fulfills the specified requirements for biodiesel without need for further refining.

44. The process according to any of the preceding items, comprising separating the oil phase/hydrophobic phase from hydrophilic phase to provide a composition comprising at least 90% (w/w) fatty acid alkyl esters, from 300 to 400 ppm soap, less than 0.25% (w/w) free fatty acids and less than 0.23% (w/w) glycerides.45. The process according to any of items 28 to 44, wherein said soap/fatty acid salts are subject to acidification to produce free fatty acids, such as by contacting the soap/fatty acid salts with HCl, $H_3PO_4$ and/or $H_2SO_4$.

46. The process according to any of items 41 to 45, wherein the free fatty acids produced by acidification of said soap/fatty acid salts are used as fatty acid feedstock in a process according to any of the preceding items.

47. The process according to any of items 41 to 46, wherein the amount of free fatty acids produced by acidification of said soap/fatty acid salts is within the range of 0.5 to 3% (w/w) of the said feedstock, such as from 1 to 2% (w/w) of the said feedstock.

48. The process according to any of the preceding items, comprising the steps of
   i) providing a reaction system comprising an oil phase/hydrophobic phase and a hydrophilic phase; e.g. a reaction system, wherein the oil phase/hydrophobic phase comprises a fatty acid feedstock containing free and/or glyceride bound fatty acids, and the hydrophilic phase comprises water, one or more lipolytic enzymes, and optionally glycerol;
   ii) adding alcohol, such as a C1-C5 alcohol, preferably ethanol or methanol, to said reaction system either step-wise or continuously, to reach an amount, which is within the range of 14 to 24% (w/w) relative to the oil phase/hydrophobic phase;
   iii) subjecting the fatty acid feedstock and the one or more lipolytic enzymes to conditions allowing transesterification of said free and/or glyceride bound fatty acids to provide a composition comprising fatty acid alkyl esters;
   iv) contacting said composition with an alkaline agent/base under conditions allowing formation of fatty acid salts/soap from residual free fatty acids in the composition; and
   v) separating the fatty acid alkyl esters from the fatty acid salts/soap.

49. The process according to any of the preceding items, comprising
  i) providing a system comprising said oil phase/hydrophobic phase and said hydrophilic phase,
  ii) reacting a fatty acid feedstock present in said oil phase/hydrophobic phase with alcohol in the presence of water and one or more lipolytic enzymes to produce said fatty acid alkyl esters and said free fatty acids.
  iii) subjecting the oil phase/hydrophobic phase and the hydrophilic phase to alkaline treatment so as to form soap/fatty acid salts of free fatty acids present in the oil phase/hydrophobic phase
  iv) separating the fatty acid alkyl esters from the hydrophilic phase containing said soap/fatty acid salts
  v) subjecting said hydrophilic phase to acidification, e.g. by addition of $H_2SO_4$.

50. The process according to any of the preceding items, wherein said soap/fatty acid salts are neutralized/subject to acidification, e.g. by addition of $H_2SO_4$ or $H_3PO_4$, so as to form salt, such as $Na_2SO_4$ or $K_2SO_4$, which precipitates in the glycerol.

51. The process according to item 50, comprising separating the precipitated salt from the glycerol, e.g. by filtration.

52. The process according to any of the preceding items, comprising drying said glycerol so as to remove e.g. water and alcohol, such as methanol, from the glycerol.

53. The process according to any of items 50 to 52, wherein said glycerol is purified, such as by drying and/or removal of alcohol, and or by filtration to produce a composition, wherein the content of glycerol is above 95% (w/w), such as above 97% (w/w), above 97.5% (w/w), above 98% (w/w), above 98.5% (w/w), above 99% (w/w), above 99.5% (w/w), above 99.75% (w/w), above 99.8% (w/w) or is above 99.9% (w/w).47. The process according to any of the preceding items wherein said fatty acid feedstock is reacted with alcohol in the presence of an amount of glycerol corresponding to 2 to 30% (w/w) relative to the oil phase/hydrophobic phase, an amount of water corresponding to 1.5 to 5.0% (w/w) relative to the oil phase/hydrophobic phase and an amount of alcohol, such as methanol, which is within the range of 14 to 24% (w/w) relative to the oil phase/hydrophobic phase.

54. The process according to any of the preceding items, wherein said alcohol is added over a period of 1 to 30 hours, such as over a period of 1 to 20 hours, e.g. a period of 16 hours.

55. The process according to any of the preceding items, wherein said fatty acid feedstock comprises or consists essentially of corn oil or distiller's corn oil.

56. A composition comprising at least 90% (w/w) fatty acid alkyl esters, from 300 to 400 ppm soap, less than 0.25% (w/w) free fatty acids and less than 0.23% (w/w) glycerides.

57. The composition according to item 50, said composition being obtainable by the process according to any of items 1 to 55.

58. The composition according to any of items 55 to 57, said composition being obtainable by a process, wherein said fatty acid feedstock comprises or consists essentially of corn oil and the said alkaline agent is KOH.

59. A composition comprising glycerol, said composition being obtainable by the process defined in any of items 1 to 46, wherein said soap/fatty acid salts are subject to acidification by contacting the soap/fatty acid salts with $H_3PO_4$ and/or $H_2SO_4$, to produce free fatty acids and salt such as $Na_2SO_4$ or $K_2SO_4$.

60. The composition according to item 59, wherein the process comprises separating the salt from the glycerol, e.g. by filtration.

61. The composition according to item 59 or 60, wherein the process comprises drying and/or reducing the amount of alcohol, such as methanol, in said glycerol.56. The composition according to item 55, wherein the content of glycerol is above 95% (w/w), such as above 97% (w/w), above 97.5% (w/w), above 98% (w/w), above 98.5% (w/w), above 99% (w/w), above 99.5% (w/w), above 99.75% (w/w), above 99.8% (w/w) or is above 99.9% (w/w).

The present invention is further described by the following examples that should not be construed as limiting the scope of the invention.

Example 1

Fatty acid methyl esters (FAME) were produced by transesterification of distiller's corn oil using low dosage of liquid lipase (SEQ ID NO: 1) of 300 LU per gram of oil.

In the experiment, glycerol and water concentrations were varied (see table 1).

TABLE 1

| Trial | % water* | % glycerol* |
|---|---|---|
| reference | 2 | 0 |
| Low Water | 1.5 | 0 |
| High Glycerol | 2 | 10 |
| High Glycerol + low water | 1.5 | 10 |
| Medium Water | 1.75 | 0 |
| Medium Glycerol | 2 | 5 |

*% w/w dosings based on oil 100 ml squared glass flasks were used as reactors and the procedure used was the following:

32 g of oil was added followed by addition of 100 ppm NaOH dissolved in demineralized water. The mixture was mixed at 35° C. and 250 rpm for 10 minutes followed by addition of glycerol and liquid lipase. The reaction was started by adding 0.70 g methanol followed by continuous dosing of 4.17 g methanol over 16 hours.

The reaction was carried out in an Innova incubator at 35° C. and 250 rpm. Reaction time per batch was 24 hours.

Yield of fatty acid methyl esters in oil phase/hydrophobic phase was quantified by gas chromatography and the content of free fatty acid was measured by NaOH titration method.

TABLE 2

| Trial | % FAME@24 h | % FFA@24 h |
|---|---|---|
| Reference | 84.8 | 2.2 |
| Low water | 78.6 | 2.1 |
| High Glycerol | 89.1 | 1.3 |
| High Glycerol and low water | 86.4 | 1.2 |
| Medium water | 81.4 | 2.1 |
| Medium glycerol | 84.5 | 1.6 |

The highest yield expressed as total FAME and lowest possible free fatty acid content was achieved with addition of 10% glycerol and 1.5-2.0% water (w/w of oil).

Example 2

Fatty acid methyl esters (FAME) were produced by transesterification of distiller's corn oil using low dosage of liquid lipase of 300 LU per gram of oil. The enzymatic reactions were carried out in 1 L stirred jacked glass reactors at 35° C. and 530 rpm over 24 hours.

The procedure used was the following:

700 g of oil was added 1.7 g 1N NaOH and 8.75 g of demineralized water. The mixture was mixed at 35 C and 530 rpm for 10 minutes followed by addition of 70.0 g glycerol and 300 LU liquid lipase (SEQ ID NO: 1) per g of oil. The reaction was started by adding 19.2 g methanol followed by continuous dosing of 115.0 g methanol over 16 hours.

Yield of fatty acid methyl esters and bound glycerol content in oil phase/hydrophobic phase was quantified by gas chromatography and the content of free fatty acid was measured by NaOH titration method.

TABLE 3

| % FAME in oil phase/ hydrophobic phase | % FFA in oil phase/ hydrophobic phase | % Bound glycerol |
|---|---|---|
| 93.3 | 1.3 | 0.87 |

The mixture was heated up to 60° C. and continuously added 28 ml of 3N KOH over 3 minutes at 530 rpm. Then temperature was increased to 82 C for 2 hours. Samples of the mixture were taken after 1 and 2 hours and centrifuged at 2000 rpm for 10 minutes and oil phase/hydrophobic phase was analyzed for fatty acid methyl ester, free fatty acid and bound glycerol content.

TABLE 4

| Time, hours | % FAME in oil phase/ hydrophobic phase | % FFA in oil phase/ hydrophobic phase | % Bound glycerol |
|---|---|---|---|
| 1 | 97.0 | 0.16 | 0.54 |
| 2 | 97.4 | 0.14 | 0.53 |

Heating and agitation were shut off and the mixture was settling for 1 hour before fatty acid methyl ester, free fatty acid, bound glycerol and soap content was measured in oil phase/hydrophobic phase.

TABLE 5

| % FAME in oil phase/ hydrophobic phase | % FFA in oil phase/ hydrophobic phase | % Bound glycerol | ppm Soap |
|---|---|---|---|
| 97.4 | 0.14 | 0.53 | 372 |

Example 3

The lipase of SEQ ID NO: 2 was used in large scale trials for testing the application for biodiesel. The enzyme was used at two levels of dosing and compared to a standard production using the lipase set forth in SEQ ID NO: 1. Production was taking place in 10,000 gal reactors and four batches were made for each series of tests. Batch number one 30 gal of the formulated enzyme with an activity of 181 LCLU/g was added; corresponding to 17 mg enzyme protein/100 g oil. No extra enzyme added in the next batches B, C, and D. Methanol was added during the first 10 hours with an amount to keep the methanol concentration in the heavy phase at approximately 15%. This addition corresponds to 1.5 molar equivalents to fatty acids in batch A and a little less in consecutive batches (approx. 1.2 equivalents). After all batches the mixing was stopped and the heavy phase was settled to the bottom of the tank for re-suspension in the next batch. From batch B only, approximately 650 gal of heavy phase was drained from the bottom of the tank after reaction and settling. The temperature for the trials using the lipase of SEQ ID NO: 2 is kept higher to utilize the higher heat tolerance of this enzyme.

TABLE 6

1st 30 gal enzyme (SEQ ID NO: 2) added

| Batch # | Oil, gallons | Reaction time, hr | Bound by GC, % | Avg temp (F.) | Final FFA % |
|---|---|---|---|---|---|
| V4-2014-218A | 7502 | 20.8 | 0.28 | 104.5 | 2.4 |
| V4-2014-219B | 6509 | 19 | 0.22 | 100.9 | 2.25 |
| V4-2014-220C | 6802 | 15.2 | 0.27 | 98.4 | 2.38 |
| V4-2014-201D | 6200 | 17.3 | 0.26 | 98.6 | 2.29 |

TABLE 7

20 gal enzyme (SEQ ID NO: 2) added

| Batch # | Oil, gallons | Reaction time, hr | Bound by GC, % | Avg temp (F.) | Final FFA % |
|---|---|---|---|---|---|
| V4-2014-206A | 7624 | 21.8 | 0.28 | 105 | 2.24 |
| V4-2014-207B | 6500 | 13.9 | 0.29 | 101.6 | 2.53 |
| V4-2014-208C | 6810 | 13.0 | 0.27 | 92.4 | 1.84 |
| V4-2014-209D | 6518 | 12.0 | 0.25 | 99.4 | 1.9 |

TABLE 8

50 gal SEQ ID NO: 1 Control with 5 gal added at batch B, C, and D

| Batch # | Oil, gallons | Reaction time, hr | Bound by GC, % | Avg temp (F) | Final FFA % |
|---|---|---|---|---|---|
| V4-2014-181A | 7506 | 20 | 0.29 | 91.7 | 2.32 |
| V4-2014-182B | 6501 | 17.5 | 0.29 | 91.4 | 1.86 |
| V4-2014-183C | 6801 | 15.6 | 0.26 | 92.7 | 2.31 |
| V4-2014-184D | 6203 | 13.5 | 0.27 | 92.4 | 2 |

SEQUENCE LISTING

<160> NUMBER OF SEQ ID NOS: 2

<210> SEQ ID NO 1

```
<211> LENGTH: 269
<212> TYPE: PRT
<213> ORGANISM: Thermomyces lanuginosus

<400> SEQUENCE: 1

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265

<210> SEQ ID NO 2
<211> LENGTH: 269
<212> TYPE: PRT
<213> ORGANISM: Artificial sequence
<220> FEATURE:
<223> OTHER INFORMATION: Lipase variant

<400> SEQUENCE: 2

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Arg Ala Pro Ala Gly Thr
            20                  25                  30

Asn Ile Thr Cys Thr Ala Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60
```

-continued

| | | | | | | | | | | | | | | | |
|---|---|---|---|---|---|---|---|---|---|---|---|---|---|---|---|
| Gly<br>65 | Phe | Leu | Ala | Leu<br>70 | Asp | Asn | Thr | Asn | Lys<br>75 | Leu | Ile | Val | Leu | Ser | Phe<br>80 |
| Arg | Gly | Ser | Arg | Ser<br>85 | Ile | Glu | Asn | Trp | Ile<br>90 | Gly | Asn | Leu | Asn | Phe<br>95 | Glu |
| Leu | Lys | Glu | Ile<br>100 | Asn | Asp | Ile | Cys | Ser<br>105 | Gly | Cys | Arg | Gly | His<br>110 | Ala | Gly |
| Phe | Thr | Ser<br>115 | Ser | Trp | Arg | Ser | Val<br>120 | Ala | Asp | Thr | Leu | Arg<br>125 | Gln | Lys | Val |
| Glu | Asp<br>130 | Ala | Val | Arg | Glu | His<br>135 | Pro | Asp | Tyr | Arg | Val<br>140 | Val | Phe | Thr | Gly |
| His<br>145 | Ser | Leu | Gly | Gly | Ala<br>150 | Leu | Ala | Thr | Val | Ala<br>155 | Gly | Ala | Asp | Leu | Arg<br>160 |
| Gly | Asn | Lys | Tyr | Asp<br>165 | Ile | Asp | Val | Phe | Ser<br>170 | Tyr | Gly | Ala | Pro<br>175 | Arg | Val |
| Gly | Asn | Arg | Ala<br>180 | Phe | Ala | Glu | Phe | Leu<br>185 | Thr | Val | Gln | Thr | Gly<br>190 | Gly | Thr |
| Leu | Tyr | Arg<br>195 | Ile | Thr | His | Thr | Asn<br>200 | Asp | Ile | Val | Pro | Arg<br>205 | Leu | Pro | Pro |
| Arg | Glu<br>210 | Phe | Gly | Tyr | Ser | His<br>215 | Ser | Ser | Pro | Glu | Tyr<br>220 | Trp | Ile | Lys | Ser |
| Gly<br>225 | Thr | Leu | Val | Pro | Val<br>230 | Arg | Arg | Arg | Asp | Ile<br>235 | Val | Lys | Ile | Glu | Gly<br>240 |
| Ile | Asp | Ala | Thr | Gly<br>245 | Gly | Asn | Asn | Gln | Pro<br>250 | Asn | Ile | Pro | Ser | Ile<br>255 | Thr |
| Ala | His | Leu | Trp<br>260 | Tyr | Phe | Gly | Leu | Ile<br>265 | Gly | Thr | Cys | Leu | | | |

The invention claimed is:

1. A process for production of fatty acid alkyl esters, comprising
   (a) reacting a fatty acid feedstock with an alcohol in the presence of one or more lipolytic enzymes and water, in a system comprising a hydrophobic phase and a hydrophilic phase, to produce fatty acid alkyl esters, free fatty acids and glycerol;
   (b) after step (a), adding an alkaline agent to the system to form soap, wherein the alkaline agent is added in an amount corresponding to 1.0-2.0 molar equivalents to the amount of free fatty acids, and
   (c) after step (b), separating the hydrophobic phase from the hydrophilic phase.

2. The process of claim 1, wherein at least 60% (w/w) of the fatty acid acyl groups or free fatty acids in the fatty acid feedstock are converted to fatty acid alkyl esters in step (a).

3. The process of claim 1, wherein the one or more lipolytic enzymes is/are lipases.

4. The process of claim 1, wherein the total amount of the one or more lipolytic enzymes is within the range of 0.005-5 g enzyme protein (EP)/kg oil or fatty acid feedstock.

5. The process of claim 1, wherein the alcohol is methanol.

6. The process of claim 1, wherein the fatty acid feedstock is derived from one or more of algae oil, canola oil, coconut oil, castor oil, copra oil, corn oil, distiller's corn oil, cottonseed oil, flax oil, fish oil, grape seed oil, hemp oil, jatropha oil, jojoba oil, mustard oil, canola oil, palm oil, palm stearin, palm olein, palm kernel oil, peanut oil, rapeseed oil, rice bran oil, safflower oil, soybean oil, sunflower oil, tall oil, oil from halophytes, animal fat, palm oil free fatty acid distillate, soy oil free fatty acid distillate, soap stock fatty acid material, yellow grease, brown grease, and any combination thereof.

7. The process of claim 1, wherein the fatty acid feedstock is derived from one or more oils selected from the group consisting of rapeseed oil, rice bran oil, safflower oil, soybean oil, sunflower oil, and any combination thereof.

8. The process of claim 1, wherein the alkaline agent is KOH, NaOH or a mixture thereof.

9. The process of claim 1, wherein the alkaline agent is sodium methoxide, potassium methoxide, or a mixture thereof.

10. The process of claim 1, wherein step (b) is performed at a temperature within the range of 35 to 45° C.

11. The process of claim 1, further comprising acidification of the soap to produce free fatty acids and salt, wherein the salt precipitates in the glycerol.

12. The process of claim 11, wherein the acidification is performed with $H_2SO_4$.

13. The process of claim 11, further comprising purifying the glycerol by drying to remove water and the alcohol, and by filtration to remove the salt, to produce a composition, wherein the content of glycerol is above 95% (w/w).

14. The process of claim 1, wherein the amount of glycerol is in the range of 2 to 30% (w/w) relative to the hydrophobic phase, the amount of water is in the range of 1.5 to 5.0% (w/w) relative to the hydrophobic phase, and the amount of the alcohol is in the range of 14 to 24% (w/w) relative to the hydrophobic phase.

* * * * *